United States Patent
Birk

(10) Patent No.: US 9,877,860 B2
(45) Date of Patent: Jan. 30, 2018

(54) BARIATRIC DEVICE AND METHOD FOR WEIGHT LOSS

(75) Inventor: Janel Birk, Oxnard, CA (US)

(73) Assignee: Apollo Endosurgery US, Inc., Austin, TX (US)

( * ) Notice: Subject to any disclaimer, the term of this patent is extended or adjusted under 35 U.S.C. 154(b) by 200 days.

(21) Appl. No.: 13/503,252

(22) PCT Filed: Oct. 26, 2010

(86) PCT No.: PCT/US2010/054165
§ 371 (c)(1),
(2), (4) Date: Apr. 20, 2012

(87) PCT Pub. No.: WO2011/056608
PCT Pub. Date: May 12, 2011

(65) Prior Publication Data
US 2012/0203061 A1 Aug. 9, 2012

Related U.S. Application Data

(60) Provisional application No. 61/255,045, filed on Oct. 26, 2009, provisional application No. 61/382,850, filed on Sep. 14, 2010.

(51) Int. Cl.
*A61F 2/04* (2013.01)
*A61F 5/00* (2006.01)

(52) U.S. Cl.
CPC .................... *A61F 5/0079* (2013.01)

(58) Field of Classification Search
CPC ...... A61F 5/0076; A61F 5/0053; A61F 5/005; A61F 5/004; A61F 5/0036; A61F 5/0013; A61F 5/0003; A61F 5/003; A61F 2002/045; A61F 2002/044; A61F 2/02; A61F 2/04; A61F 5/0079; A61F 2/0063; A61M 25/04; A61M 29/00; A61M 29/02
USPC ............. 606/191; 623/23.64–23.65; 424/551
See application file for complete search history.

(56) References Cited

U.S. PATENT DOCUMENTS

| | | | | |
|---|---|---|---|---|
| 4,846,836 A * | 7/1989 | Reich | | 623/23.68 |
| 6,322,538 B1 * | 11/2001 | Elbert | | A61J 15/0015 604/105 |
| 6,764,518 B2 * | 7/2004 | Godin | | 623/23.68 |
| 6,845,776 B2 * | 1/2005 | Stack | | A61F 2/04 128/898 |
| 6,960,233 B1 * | 11/2005 | Berg | | A61F 2/04 623/23.64 |
| 7,708,684 B2 * | 5/2010 | Demarais et al. | | 600/37 |

(Continued)

FOREIGN PATENT DOCUMENTS

| WO | 2005094257 A2 | 10/2005 | |
|---|---|---|---|
| WO | WO 2008101048 A2 * | 8/2008 | A61F 2/04 |

*Primary Examiner* — Anh Dang
*Assistant Examiner* — Erin Colello
(74) *Attorney, Agent, or Firm* — Gordon & Jacobson, P.C.

(57) ABSTRACT

A bariatric device for use in inducing weight loss, comprising a cardiac element and a fixation element wherein the fixation element attaches the cardiac element to the upper stomach to allow the cardiac element to apply at least intermittent pressure to the upper stomach which produces a satiety signal to the user, giving the recipient a feeling of fullness and reducing his or her hunger feelings. The device may also contain an esophageal element which is connected to the cardiac element by a connecting element.

12 Claims, 22 Drawing Sheets

(56) References Cited

U.S. PATENT DOCUMENTS

| | | | |
|---|---|---|---|
| 7,846,174 B2* | 12/2010 | Baker | A61F 2/04 606/191 |
| 7,981,162 B2* | 7/2011 | Stack | A61F 2/04 604/8 |
| 8,100,931 B2* | 1/2012 | Baker et al. | 606/191 |
| 8,529,431 B2* | 9/2013 | Baker | A61B 17/00234 600/37 |
| 9,060,844 B2* | 6/2015 | Kagan | A61F 2/04 |
| 2003/0040808 A1* | 2/2003 | Stack | A61F 2/04 623/23.65 |
| 2003/0093117 A1* | 5/2003 | Saadat | A61B 17/0401 606/221 |
| 2004/0092892 A1* | 5/2004 | Kagan | A61F 2/04 604/264 |
| 2004/0138761 A1* | 7/2004 | Stack | A61F 2/04 623/23.65 |
| 2004/0143342 A1* | 7/2004 | Stack et al. | 623/23.65 |
| 2004/0172141 A1* | 9/2004 | Stack | A61F 2/04 623/23.65 |
| 2004/0220682 A1* | 11/2004 | Levine et al. | 623/23.65 |
| 2005/0096673 A1* | 5/2005 | Stack et al. | 606/151 |
| 2005/0096750 A1* | 5/2005 | Kagan | A61F 2/04 623/23.65 |
| 2005/0177181 A1* | 8/2005 | Kagan | A61B 17/00234 606/151 |
| 2005/0192629 A1* | 9/2005 | Saadat | A61F 5/0076 606/221 |
| 2005/0247320 A1* | 11/2005 | Stack et al. | 128/898 |
| 2006/0155375 A1* | 7/2006 | Kagan et al. | 623/11.11 |
| 2006/0206063 A1* | 9/2006 | Kagan et al. | 604/264 |
| 2006/0252983 A1* | 11/2006 | Lembo | A61F 5/0053 600/37 |
| 2006/0264982 A1* | 11/2006 | Viola et al. | 606/153 |
| 2007/0060932 A1* | 3/2007 | Stack | A61B 17/0469 606/153 |
| 2007/0166396 A1* | 7/2007 | Badylak | A61K 35/38 424/551 |
| 2007/0185374 A1* | 8/2007 | Kick | A61B 17/00234 600/37 |
| 2007/0208429 A1* | 9/2007 | Leahy | A61F 2/02 623/23.68 |
| 2007/0233162 A1* | 10/2007 | Gannoe | A61B 17/072 606/153 |
| 2007/0293716 A1* | 12/2007 | Baker | A61F 2/04 600/37 |
| 2008/0015523 A1* | 1/2008 | Baker | 604/288.01 |
| 2008/0208356 A1* | 8/2008 | Stack | A61F 2/04 623/23.65 |
| 2008/0228030 A1* | 9/2008 | Godin | A61B 17/0401 600/106 |
| 2008/0255678 A1* | 10/2008 | Cully | A61F 2/04 623/23.65 |
| 2009/0012553 A1* | 1/2009 | Swain | A61F 5/0076 606/191 |
| 2009/0177215 A1* | 7/2009 | Stack et al. | 606/153 |
| 2011/0264234 A1* | 10/2011 | Baker et al. | 623/23.64 |

* cited by examiner

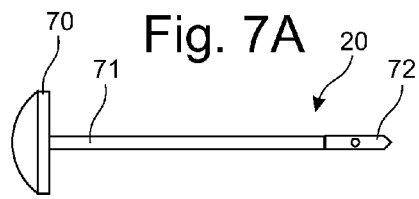
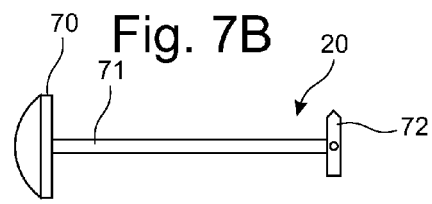
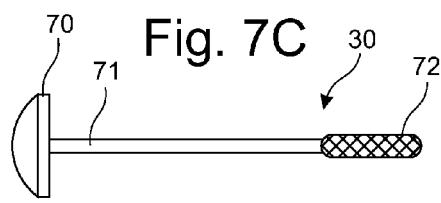
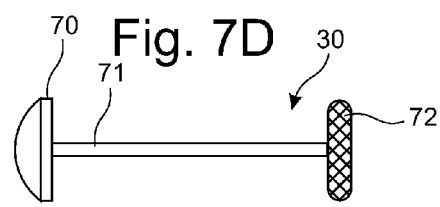
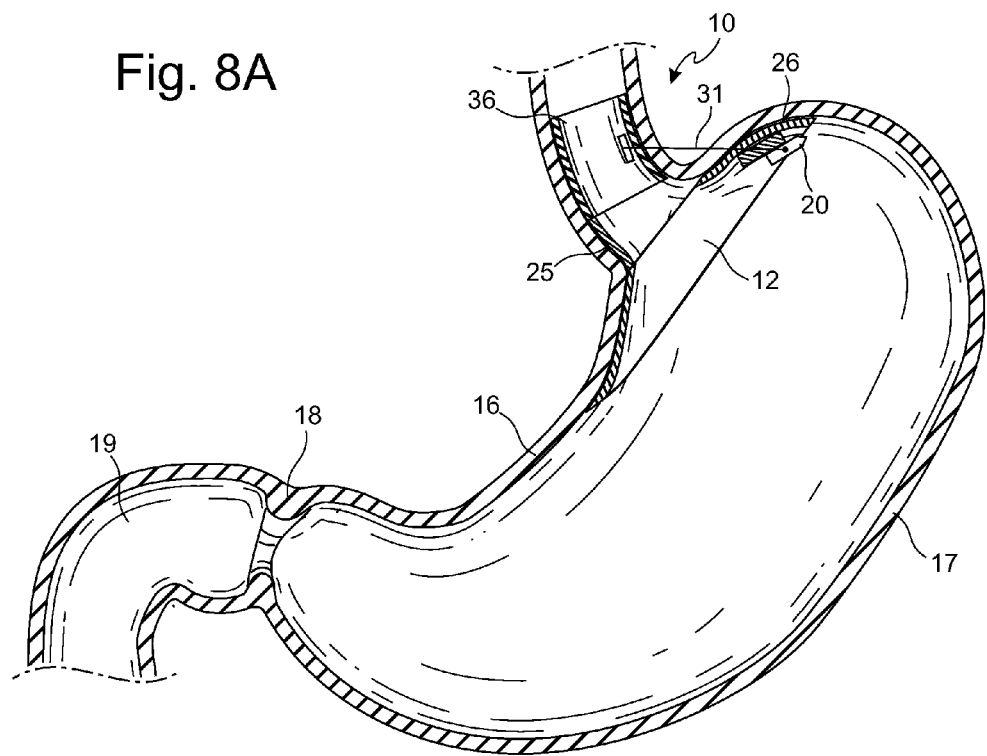

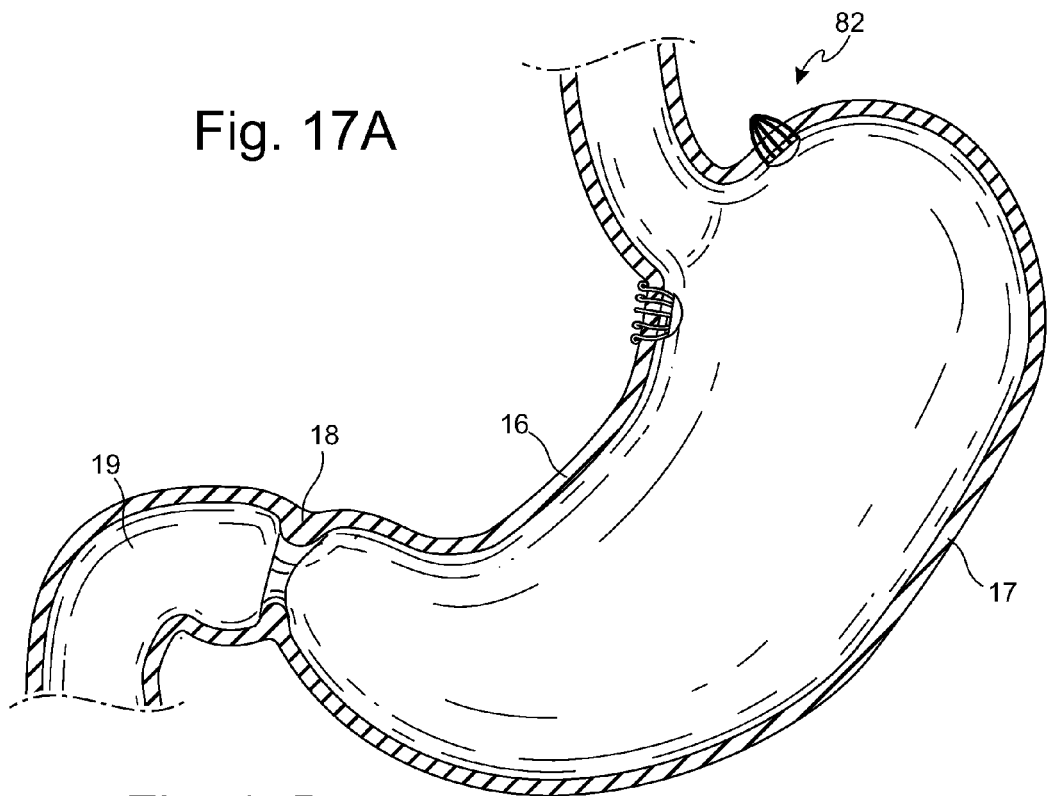
Fig. 17A
Fig. 17B
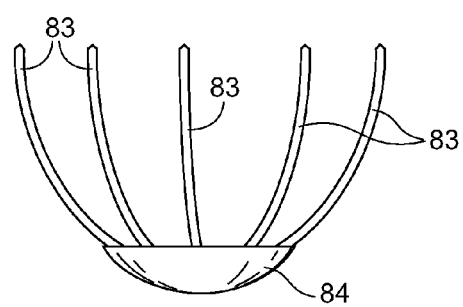
Fig. 17C
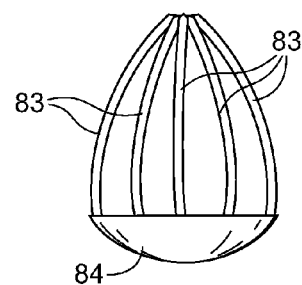
Fig. 17D
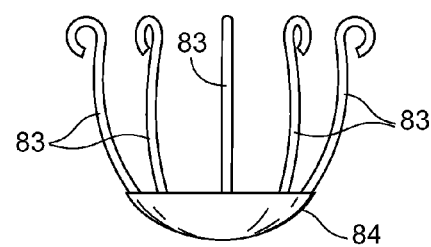

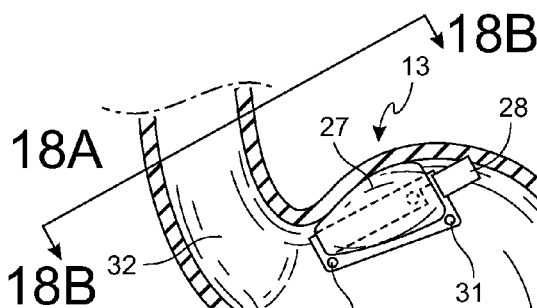
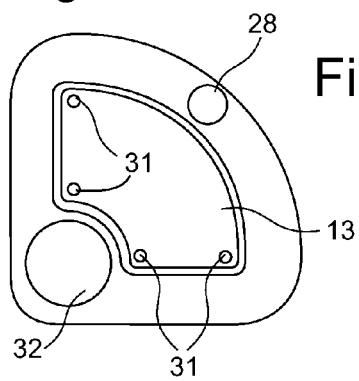
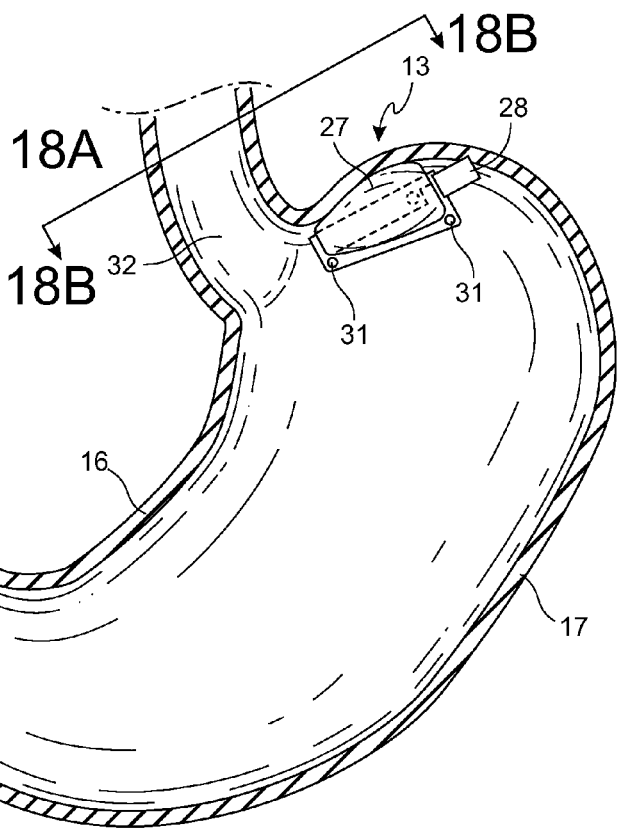
Fig. 18b
Fig. 18A
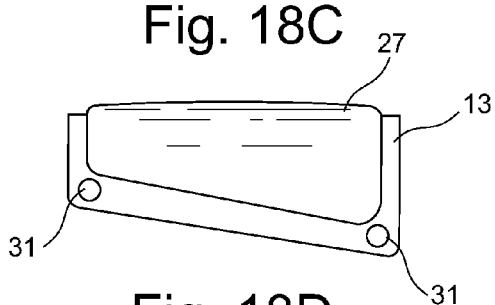
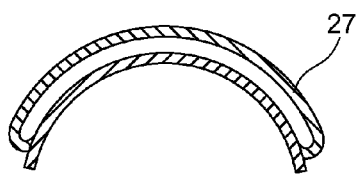
Fig. 18C
Fig. 18E
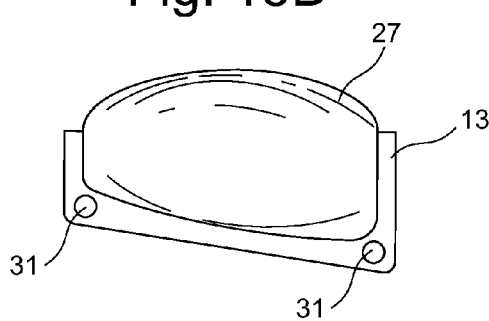
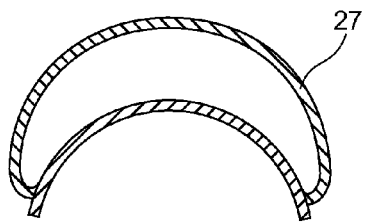
Fig. 18D
Fig. 18F

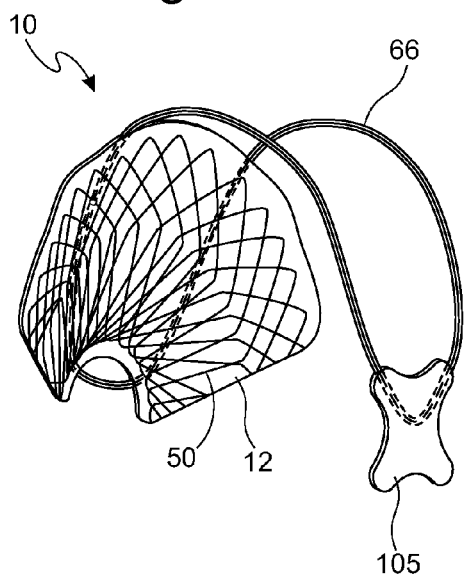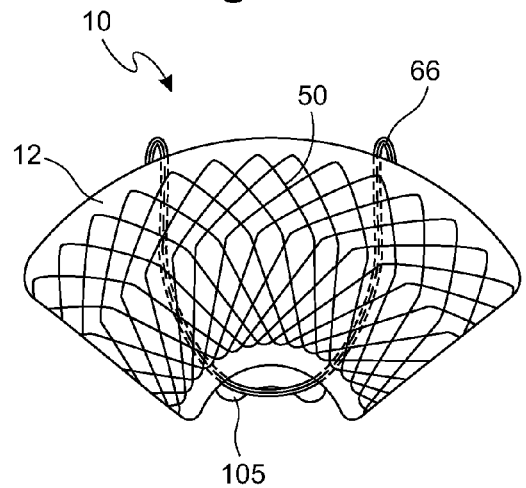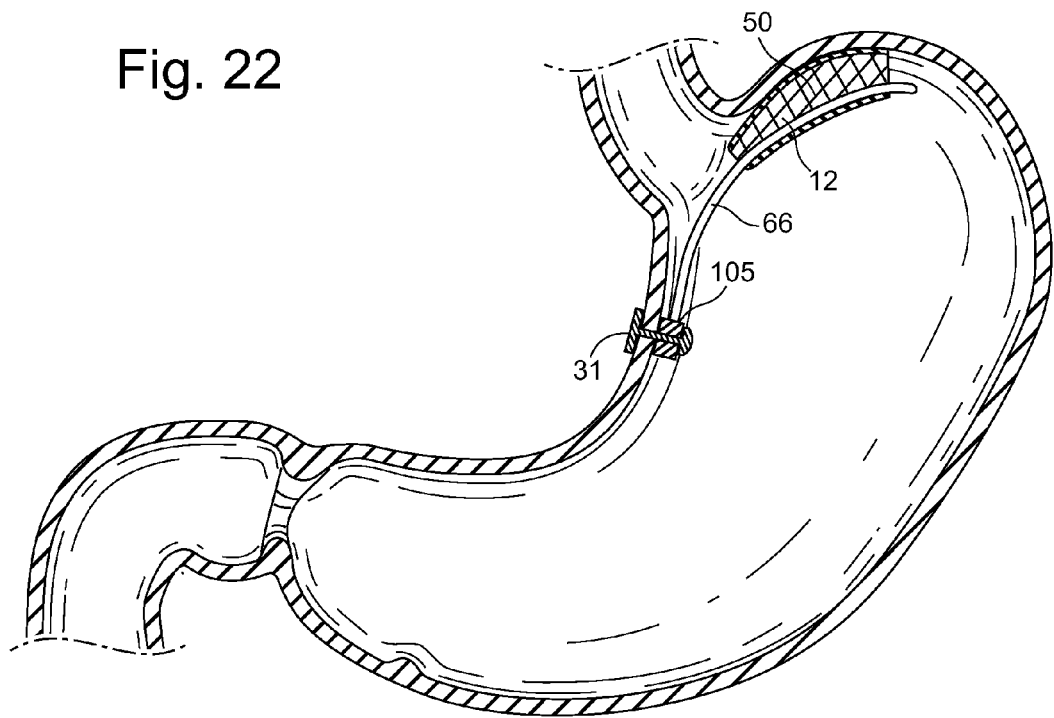

BARIATRIC DEVICE AND METHOD FOR WEIGHT LOSS

RELATED APPLICATION

This application is a national stage application under 35 USC §371 of PCT Patent Application No. PCT/US2010/054165, filed Oct. 26, 2010, which claims the benefit of U.S. Provisional Application No. 61/255,045, filed Oct. 26, 2009, and U.S. Provisional Application No. 61/382,850, filed Sep. 14, 2010.

TECHNICAL FIELD

This invention relates to a bariatric device for weight loss, and ancillary items such as sizing, and monitoring.

BACKGROUND

Obesity has been steadily increasing worldwide and poses serious health risks, which if untreated, can become life threatening. There are various methods for reducing weight such as diet, exercise, and medications but often the weight loss is not sustained. Significant advances have been made in the surgical treatment of obesity. Surgical procedures such as the gastric bypass and gastric banding have produced substantial and lasting weight loss for obese patients. These procedures and products have been shown to significantly reduce health risks over time, and are currently the gold standard for bariatric treatment.

Although surgical intervention has been shown to be successful at managing weight loss, both procedures are invasive and carry the risks of surgery. Gastric bypass is a highly invasive procedure which creates a small pouch by segmenting and/or removing a large portion of the stomach and rerouting the intestines permanently. Gastric bypass and its variations have known complications. Gastric banding is an invasive procedure which creates a small pouch in the upper stomach by wrapping a band around the stomach to segment it from the lower stomach. Although the procedure is reversible, it also carries known complications.

Less invasive or non-invasive devices that are removable and capable of significant weight loss are desirable. A device that has demonstrated less invasive approach is defined in U.S. patent application Ser. No. 11/463,192 and PCT/US2008/053912, and shows a three element or single element device that is sutured through the esophagus and cardia or the cardia. The inventions included herein demonstrate improvements of this device such as improved means of adjustability, use of sensors for monitoring physical parameters, use of sensors to controls adjustments, remote adjustments with sensor data, data storage for data collected through the sensors, improvements in fixation, shape and form, and improvements in contact area.

This application also includes new inventions for bariatric devices that apply force to the upper stomach which are placed with fixation or devices which could be placed without fixation in the pouch of a gastric band or by pass patient.

SUMMARY

The bariatric device described herein induces weight loss by engaging the upper stomach which could include the cardia, the adjacent fundus, the abdominal portion of the esophagus or the gastroesophogeal junction. One embodiment of the bariatric device disclosed herein is based on applying force or pressure on or around the gastroesophogeal (GE) junction and upper stomach. It may also include pressure in the lower esophagus. The device can be straightened or compressed to allow for introduction down the esophagus and then change into the desired shape inside the stomach. This device is then secured with sutures or other fixation to maintain the pressure against the upper stomach. The device may be constructed of a single main element with fixation and adjustability:

1) A cardiac element that contacts or intermittently contacts the upper stomach
    a. Fixation to hold the device position and location
    b. Adjustment means One of the purposes of the cardiac element which contacts the upper stomach or cardia is to at least intermittently apply direct force or pressure to this region of the stomach. Applying force or pressure to this region of the stomach replicates the forces and pressures that are generated during eating and swallowing. It also engages or stimulates the stretch receptors that are present in this region of the stomach. During eating, as the stomach fills, peristalsis starts and generates higher pressures in the stomach for digestion, which activates the stretch receptors to induce a satiety response, and may also trigger a neurohormonal response to cause satiety or weight loss. The cardiac element replicates this type of pressure on the stretch receptors. The cardiac element could take the form of many different shapes but a preferred shape is the frusto-cone. This element could take the form of many different shapes such as a ring, a disk, a cone, a frusto-cone, a portion of a cone, portion of frusto-cone, a sphere, an oval, an ovoid, a tear drop, a pyramid, a square, a rectangle, a trapezoid, a wireform, a spiral, a protuberance, multiple protuberances, multiple spheres or multiples of any shape or other suitable shapes. It could also be an inflatable balloon or contain an inflatable balloon. For the purpose of the claims of this patent, the "upper stomach" includes the cardiac region (a band of tissue in the stomach that surrounds the gastroesophogeal (GE) junction), and the fundus adjacent to the cardiac region, and may be either of these two areas, or both.

With the single cardiac member, a means of fixation will be required to hold the device in place. This could be accomplished by sutures, barbs, tacks, clips, t-connectors or others. The device could also be placed without fixation where the device may be held in place by restriction caused by a gastric band, gastric bypass, sleeve gastrectomy or other previous bariatric procedure. Where fixation is used, it could be permanently integrated into the cardiac element or it could be a separate piece that is modular to add at the time of placement. To make the device customized for each patient, a means for adjusting the amount of pressure that is placed on the cardia can be incorporated into the device.

In another embodiment of the bariatric device disclosed herein, the device may be constructed of three main elements with fixation and adjustability:

1) A cardiac element that contacts or intermittently contacts the upper stomach
2) An esophageal element located in the abdominal portion of the esophagus.
3) A connecting element to connect the first 2 elements
    a. Fixation to hold the device position and location
    b. Adjustment means One of the purposes of the cardiac element which contacts the upper stomach or cardiac region would be to apply at least intermittent pressure or force to engage a satiety response and/or cause a neurohormonal response to cause a reduction in weight. This element could take the form of many different shapes but the preferred shape is a frusto-cone. This element could take the form of many different shapes such as a ring, a disk, a cone, frusto-cone, a portion of a cone, portion of frusto-cone, a sphere, an oval, an ovoid, a tear drop, a pyramid, a square, a rectangle, a trapezoid, a wireform, a spiral, a protuberance, multiple protuberances, multiple spheres or multiples of any shape or other suitable shapes. It could also be an inflatable balloon or contain an inflatable balloon. This balloon could be spherical, or it could be a torus or a sphere with channels on the side to allow food to pass, or it could be a cone, a portion of a cone or other shapes. The cardiac element may be in constant or intermittent contact with the upper stomach based on the device moving in the stomach during peristalsis.

The purpose of the esophageal element is to also engage stretch receptors located at the lower esophagus to stimulate satiety and could also provide a means for fixation into the esophagus. Alternatively, the purpose of the esophageal element may be only to fix the device in the esophagus and/or serve as a lever for the cardiac element.

The purposes of the connecting element are to connect the cardiac and esophageal elements, to provide structure for the device to maintain its relative placement location, and to provide tension, pressure, or an outwardly biasing force on the cardiac element.

A means of fixation will be required to hold the device in place. This could be accomplished by sutures, barbs, tacks, clips, T-bars or others. The fixation could be permanently integrated into the cardiac element or it could be a separate piece that is modular to add at the time of placement.

The purpose of the adjustability of the device is to ensure that the proper amount of pressure is applied to each patient. The adjustability allows the pressure to be customized for each patient to optimize the response. If the pressure is too great, the patient may experience discomfort, nausea or a total disinterest in food. Conversely, if the pressure is too low, the patient may continue to overeat and the effectiveness of the device may be reduced. By allowing the physician to adjust the device after placement, the treatment can be customized. Similarly, patients may experience satiety in the beginning, but it may wane over time. These patients may require an adjustment to increase the satiety signal overtime, and the adjustability feature provides the device this flexibility. The adjustability could be achieved in a variety of forms. For example, it may be desirable to change the distance between the esophageal and cardiac elements to change the overall length of the device to increase compression of the cardia. For example, it may be desirable to change the distance between the esophageal and cardiac elements to change the overall length of the device to increase compression of the cardia. This could be accomplished by changing the length of the connecting element or the fixation element. It may also be desirable to change the shape of the device, such as to increase the diameter or angle of the device. The change may be to just a small area of the device. It may also be desirable to increase or decrease the stiffness of the device to increase resistance of the device against the tissue. This change may also be to just a small area of the device to gain a specific response.

The cardiac, esophageal and connecting elements could also be self-expanding or incorporate a portion that is self expanding. Self expansion would allow the element or a portion of the element to be compressible, but also allow it to expand back into its original shape to maintain its function and position within the stomach, as well as the function and position of the other element(s). Self expansion would allow the elements to compress for placement down the esophagus, and then expand to its original shape in the stomach. This may also allow the element to accommodate peristalsis once the device is in the stomach.

In any of the embodiments disclosed herein, the device may be straightened or collapsed for insertion down the esophagus, and then reformed to the desired shape in the stomach to apply pressure at the upper and lower stomach regions or other regions as described above. At least a portion of the device could be made of a shape memory alloys such as Nitinol (nickel titanium), low density polyethylene or polymers to allow for it to compress or flex and then rebound into shape in the stomach. For placement of the device into the stomach, a flexible polymer tube, such as a large diameter overtube or orogastric tube, could be placed down the esophagus to protect the esophagus and stomach. The device could then be straightened and placed into the tube for delivery into the stomach, and then regain its proper shape in the stomach once it exits the tube. Another variation for placement would be a custom delivery catheter to compress the device during placement and then allow the device to deploy out of the catheter once in the stomach.

The bariatric device could be made of many different materials. Elements of the device could be made with materials with spring properties that have adequate strength to hold their shape after reforming, and/or impart an outwardly biasing force. The materials would also need to be acid resistant to withstand the acidic environment of the stomach. Elements of the device could be made of Nitinol, shape memory plastics, shape memory gels, stainless steel, superalloys, titanium, silicone, elastomers, teflons, polyurethanes, polynorborenes, styrene butadiene co-polymers, cross-linked polyethylenes, cross-linked polycyclooctenes, polyethers, polyacrylates, polyamides, polysiloxanes, polyether amides, polyether esters, and urethane-butadiene co-polymers, other polymers, or combinations of the above, or other suitable materials. For good distribution of stress to the stomach wall or to reduce contact friction, the device could be coated with another material or could be placed into a sleeve of acid resistant materials such as teflons, PTFE, ePTFE, FEP, silicone, elastomers or other polymers. This would allow for a small wire to be encased in a thicker sleeve of acid resistant materials to allow for a better distribution of force across a larger surface area. The device could take many forms after it reshapes.

BRIEF DESCRIPTION OF DRAWINGS

FIG. 7A depicts a side view of a T-bar in the undeployed state.

FIG. 7B depicts a side view of a T-bar in the deployed state.

FIG. 7C depicts a side view of a fixation element in the undeployed state.

FIG. 7D depicts a side view of a fixation element in the deployed state.

FIG. 8A depicts a side view of an embodiment of a bariatric device of the present invention with an adjustment mechanism located within a cross-section of a stomach.

FIG. 17A depicts a side view of an embodiment of the bariatric device of the present invention, located within a cross-section of a stomach FIG. 17B depicts a side view of an embodiment of a bariatric device of the present invention in the undeployed state.

FIG. 17C depicts a side view of an embodiment of a bariatric device of the present invention in the deployed state.

FIG. 17D depicts a side view of an embodiment of a bariatric device of the present invention in the deployed state.

FIG. 18A depicts a side view of an embodiment of a bariatric device of the present invention with an adjustment mechanism, located within a cross-section of a stomach.

FIG. 18B depicts a top view of an embodiment of a bariatric device of the present invention with an adjustment mechanism, located within a cross-section of a stomach FIG. 18C depicts a side view of an embodiment a bariatric device of the present invention with an adjustment mechanism in the deflated state.

FIG. 18D depicts a side view of an embodiment of a bariatric device of the present invention with an adjustment mechanism in the inflated state.

FIG. 18E depicts a front view of an embodiment of a bariatric device of the present invention with an adjustment mechanism in the deflated state.

FIG. 18F depicts a front view of an embodiment of a bariatric device of the present invention with an adjustment mechanism in the inflated state.

FIG. 21A depicts a backside perspective view of an embodiment of the bariatric device of FIG. 20.

FIG. 21B depicts a front view of an embodiment of the bariatric device of FIG. 20.

FIG. 22 depicts a side view of an embodiment of a bariatric device of the present invention, located within a cross-section of a stomach.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
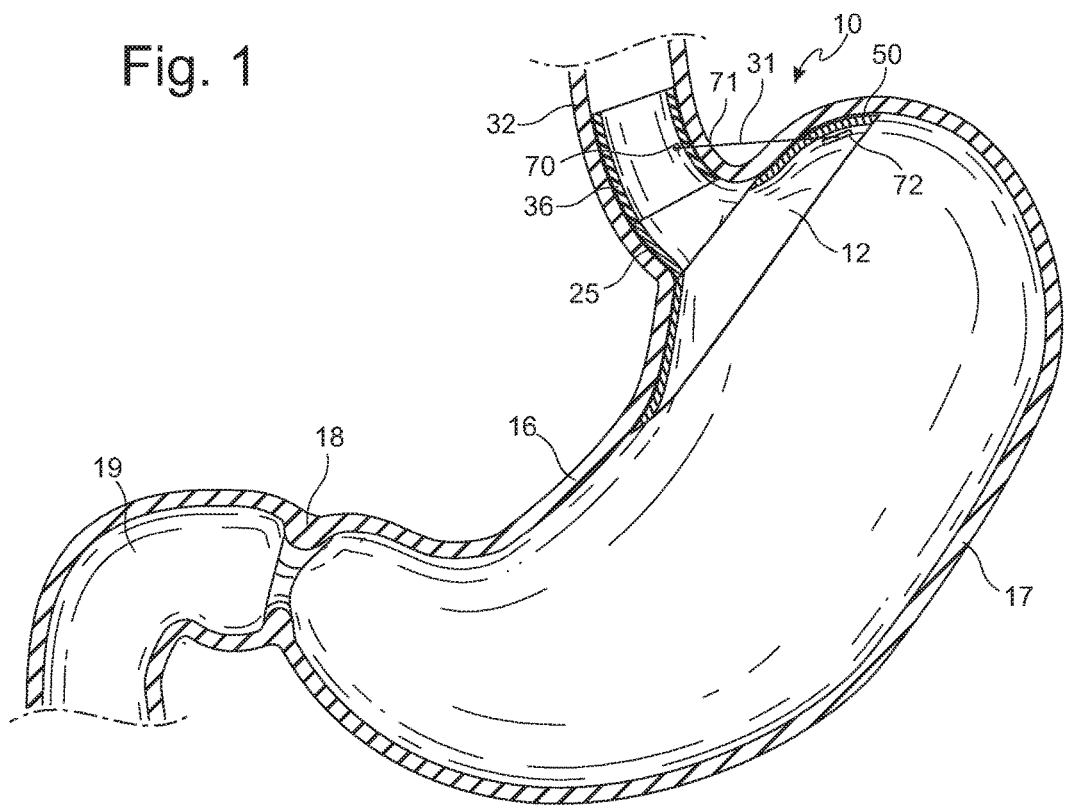
FIG. 1 depicts a side view of an embodiment of a bariatric device located within a cross-section of a stomach.
Figure 2A:
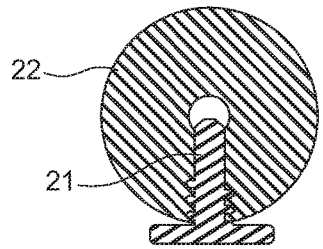
FIG. 2A depicts a front view of an adjustment mechanism for an embodiment of the present invention.
Figure 2B:
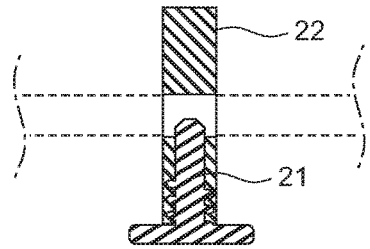
FIG. 2B depicts a side view of an adjustment mechanism for an embodiment of the present invention.
Figure 2C:
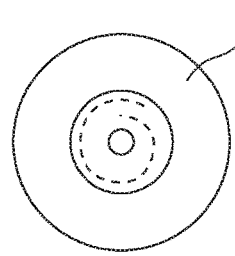
FIG. 2C depicts a front view of an adjustment mechanism for an embodiment of the present invention.
Figure 2D:
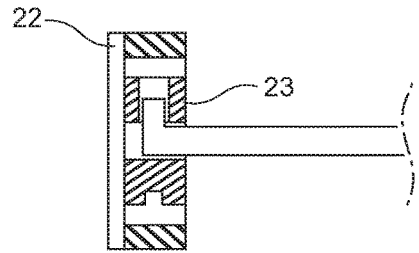
FIG. 2D depicts a side view of an adjustment mechanism for an embodiment of the present invention.

The most basic embodiment of the 3 element bariatric device 10 is shown in FIG. 1, where the device consists of an esophageal element 36, cardiac element 12, and a connecting element 25 between the esophageal and cardiac elements. In this embodiment, the esophageal and cardiac elements 36, 12 are separate structures, and do not form a contiguous surface, but instead are connected by the third separate structure, the connecting element 25. Such a non-contiguous structure may be referred to in the claims as "dis-contiguous." This device may require fixation to the stomach and/or esophagus to hold it in place to allow it to induce a satiety response and to prevent it from migrating. The fixation element 31 shown in FIG. 1 comprises a fixation connector 71 (which may be a suture or other suitable connector), coupled with the esophageal element 36 by a first anchor 70, and coupled with the cardiac element 12 by a second anchor 72. As will be discussed below, a fixation element 31 may comprise many variations and combinations of anchors and/or fixation connectors. This embodiment delivers direct force to at least one of the following 1) the abdominal portion of the esophagus 2) the esophageal-gastric junction, and 3) the proximal cardiac portion of the stomach; and the force delivered is adjustable through a variety of means to match the individual needs of the patient. To improve the ease of adjustment and the accuracy of the adjustment, the device could be adjusted by manual or automated means.

In another embodiment, the device may have a single structural element for applying force to the upper stomach or cardia. This device may be fixed into the cardia, fundus, body or pyloric region of the stomach. To further improve the satiety response of this device, it may contain an adjustment of this single element to increase or decrease the amount of force applied to the upper stomach.

The bariatric device in either the three -or single-element embodiments may be self expanding. FIG. 1 depicts an embodiment where the cardiac and esophageal elements 12, 36 are self expanding. These elements could be self expanding or have a portion that is self expanding to allow the device to flex with peristalsis, but maintain tension to spring open to apply pressure or contact and position within the stomach. The self expanding portion could be made of Nitinol, silicone, polyurethane, PTFE, Teflons, stainless steel, super alloys or other suitable materials or combinations of suitable materials. A Nitinol wire mesh pattern 50 can be applied to a frusto-conical shape to create a shell. The Nitinol wire may act as a stiffening member within the cardiac and esophageal elements 12,36. The Nitinol wire could be arranged in many different patterns to allow for the appropriate amount of self expansion while allowing the element to compress during peristalsis. The array pattern could include circular arrays, angular arrays, linear arrays, or other suitable arrays. The pattern could be woven or a continuous spiral.

The self expanding function may also assist in deployment by allowing the device to compress and then regain its shape. A preferred method of deployment is to compress the bariatric device into a long narrow shape, which is then placed in a deployment tube, sheath or catheter. The collapsed and encased device is then guided down the patient's esophagus and into the stomach, where the bariatric device is released from the deployment tube or catheter. Once released, the device would expand to its original operational shape. The stiffening member, such as Nitinol wire, may provide adequate stiffness to expand the elements into their operational shape, and maintain that general shape during operation, while allowing flexibility to accommodate peristalsis.

As mentioned above, a preferred device has adjustability or adaptability to match any changes in the patient over time. A variation of the above embodiments would be to allow the device to be adjustable via an adjustment element. This adjustability could be in the length, shape, angle or stiffness of the cardiac 12, esophageal 36, connecting 25, and/or fixation elements 31. Adjustability may be a desirable feature, whether manual or automated. For the present device, there may be numerous adjustment mechanisms. For example, it may be desirable to change the distance between the cardiac 12 and esophageal 36 elements to change the overall length of the device to increase compression of the cardia. This could be achieved by adjusting the length of the connecting element or the fixation element. For the three element device, the adjustment mechanism could be located on the esophageal, cardiac, connecting or fixation elements or any combination of the above. In all cases, the actuation mechanism could be enclosed in a sheath or tube to protect the stomach and to encase the actuation mechanism as needed. A sheath may not be required if the actuation mechanism is designed with smooth contours on its own.

Manual Adjustments:

As mentioned, the adjustment could be applied along the fixation element 31 that holds the device in place or to the connecting element 25. For example, where the fixation connector 71 is a suture, it could thread through a holding feature (an anchor 72) located inside the stomach such as a disk or button. This button (anchor 72) could contain a threaded locking pin or a spring loaded locking pin 21. See FIGS. 2A, 2B, 2C, and 2D. When an adjustment is required, the pin 21 could be released and the suture could be grasped with an instrument and pulled to change the suture length. When the proper length had been achieved, the locking pin 21 could be repositioned to lock the suture into place. The holding feature could also have a winding element 23 to allow the suture to be wound into the holding feature to reduce the length. Similarly, the suture could have positional features such as knots or bead that could be pulled through a cord stop feature and would prevent the suture from pulling backwards.

Figure 3A:
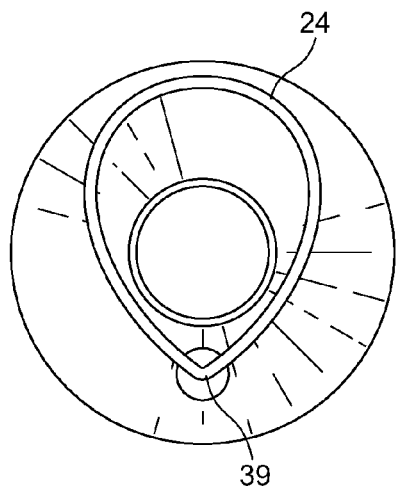
FIG. 3A depicts a top view of an embodiment of the bariatric device of the present invention.
Figure 3B:
FIG. 3B depicts a side view of an embodiment of the bariatric device of the present invention.
Figure 3C:
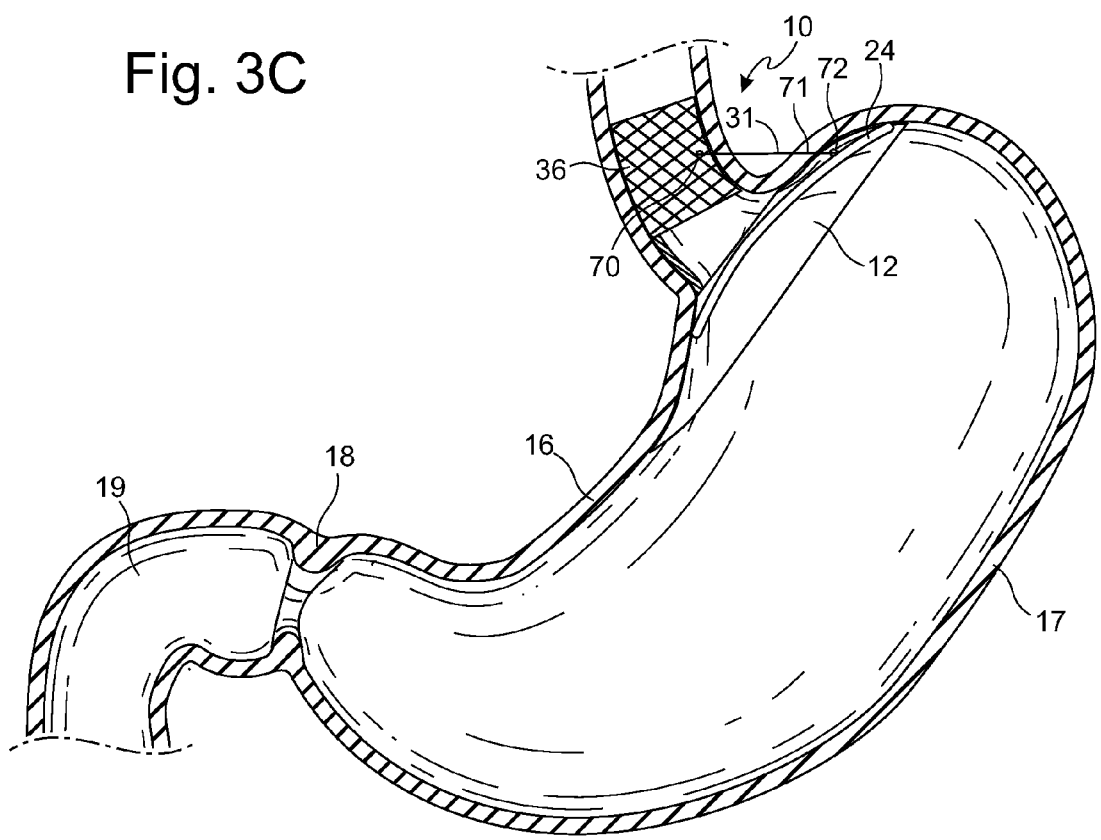
FIG. 3C depicts a side view of an embodiment of a bariatric device of the present invention located within a cross-section of a stomach.

It may also be desirable to change the shape of the device, such as to increase the diameter or angle of the device. It may also be desirable to increase or decrease the stiffness of the device to increase resistance of the device against the tissue. This could be achieved by a modular stiffening member 24 or a modular piece. See FIGS. 3A, 3B, and 3C. The stiffening member could be fixed with a suture or placed into a connection pocket, or modular connector 39 after the device was in place to add additional stiffness to the proximal cardia. The stiffening member 24 could be in the shape of a tear drop or oval and be relatively flat in profile. The stiffener could be placed on the outside or inside surface of the cardiac element. When the stiffener was connected to the device it will flex to the curvature of the cardia and fundus and act like a spring to apply additional pressure against the proximal cardia or upper stomach. The preferred material for this member would be Nitinol, but could be made from other materials. This member could be made of a variety of shapes, profiles and stiffnesses. This feature could also be achieved by applying a spacer or conical liner 26 to the existing cardiac element. This piece could have a different profile or stiffness and attach to the existing fixation to apply to greater force to increase resistance.

Figure 4A:
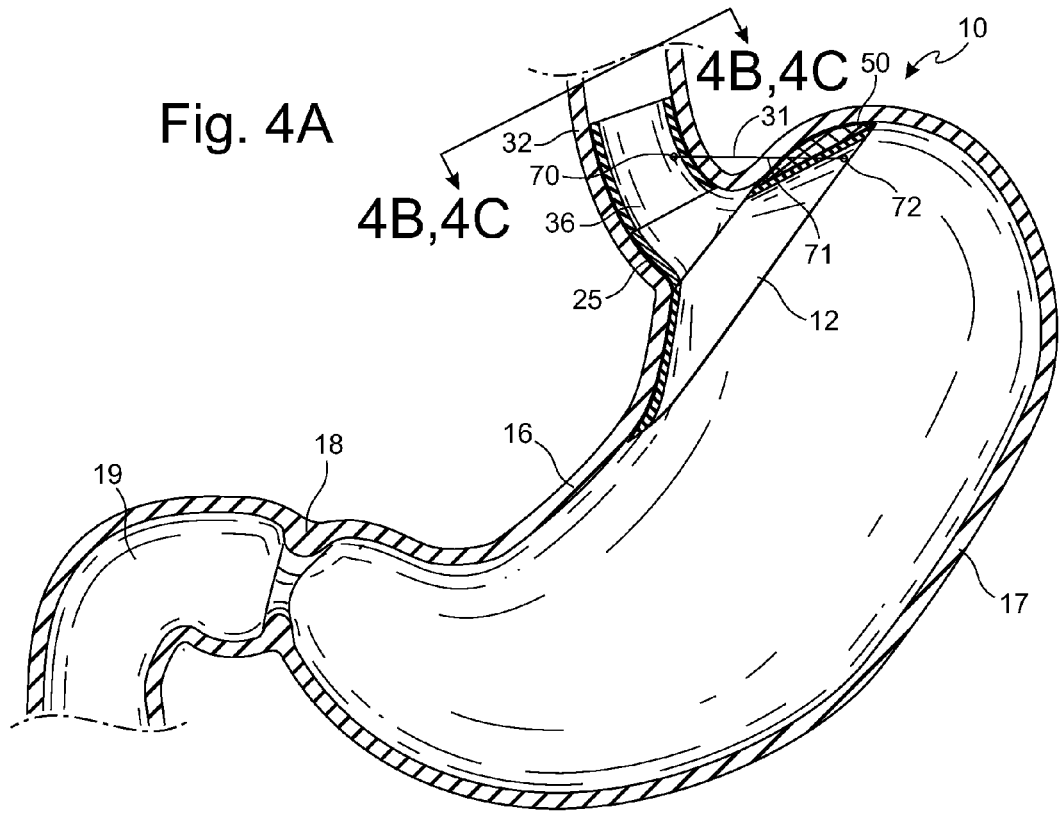
FIG. 4A depicts a side view of an embodiment of a bariatric device of the present invention located within a cross-section of a stomach with a modular adjustment mechanism.
Figure 4B:
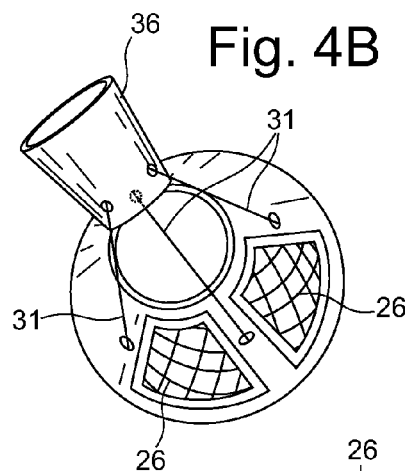
FIG. 4B depicts a top view of an embodiment of the bariatric device of the present invention with 2 modular adjustment mechanisms.
Figure 4C:
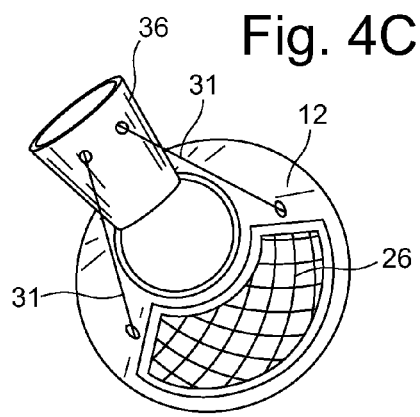
FIG. 4C depicts a top view of an embodiment of the bariatric device of the present invention with 1 modular adjustment mechanism.
Figure 4D:
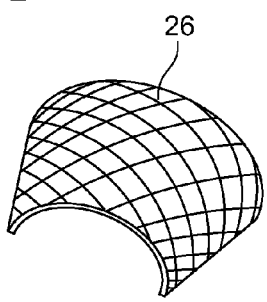
FIG. 4D depicts a front perspective view of a modular adjustment mechanism from FIG. 4A.
Figure 4E:
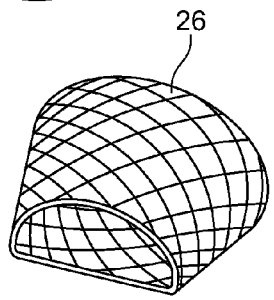
FIG. 4E depicts a front perspective view of a modular adjustment mechanism from FIG. 4A.

Another variation of this embodiment would be to allow spacers 26 to be placed in between the cardiac element and the cardiac wall. Such a spacer 26 may fit into a pocket or feature of the cardiac element to apply outward force for additional pressure against the cardia. The spacers could be made from solid or hollow sections of polymers, silicone, foam, wire mesh or the like. The spacers could also be constructed of self expanding Nitinol features or springs that could apply pressure to the cardia or upper stomach, but give during peristalsis. See FIGS. 4A, 4B, and 4C. These self expanding Nitinol spacers 26 could have a variety cross-sectional shapes, angles, and resistance to allow for a range of compression to be applied to the cardia. See FIGS. 4D, and 4E. Such Nitinol spacers 26 may be wire mesh, coated wire mesh, a wire mesh incorporated into a material such as silicone, or other suitable construction to maintain its shape while retaining some flexibility. FIG. 4B shows an example where multiple spacers 26 could be used to fit in between the fixation element 31 or one large spacer 26 could be used as shown in FIG. 4C. The spacer 26 could be removed endoscopically with a collapsing drawstring and then replaced with a different spacer 26 to change the amount of pressure applied to the cardia or upper stomach. As shown in FIGS. 4D and 4E, the spacer 26 could be self expanding material, shaped like a one sided arch, a hemicone, a hemi-frusto-cone, a generally conical shape or other suitable shapes.

Figure 5A:
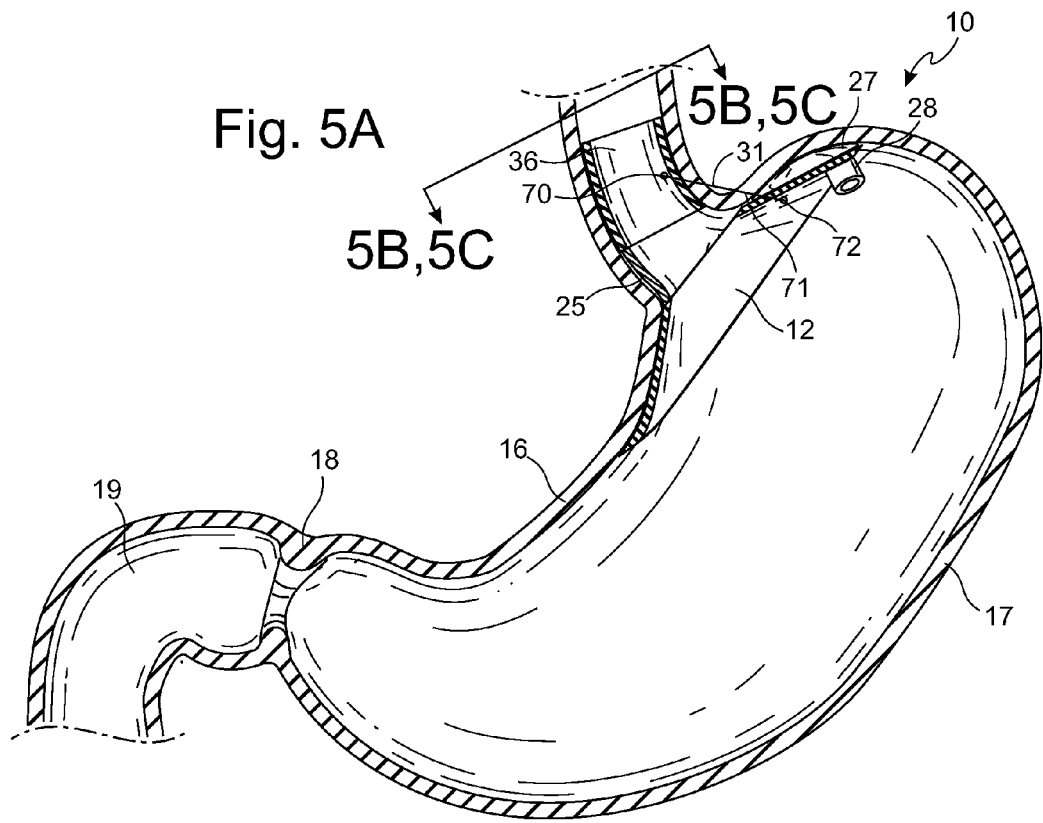
FIG. 5A depicts a side view of an embodiment of the bariatric device of the present invention with an adjustment mechanism located within a cross-section of a stomach.
Figure 5B:
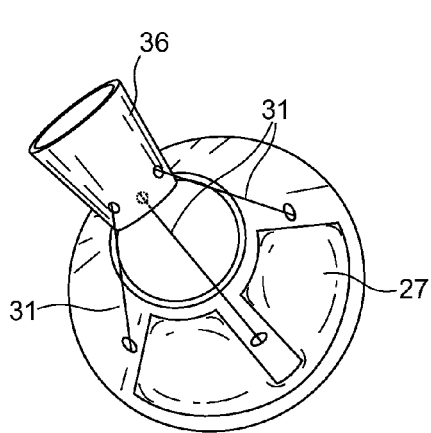
FIG. 5B depicts a top view of an embodiment of a bariatric device of the present invention with an adjustment mechanism.
Figure 5C:
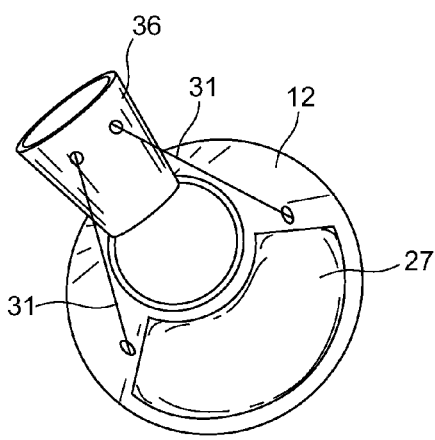
FIG. 5C depicts a top view of an embodiment of a bariatric device of the present invention with an adjustment mechanism.

Another variation would be to have a spacer 26 in the form of an inflatable body 27 attached to the top of the cardiac element in the cardia or upper stomach. See FIGS. 5A, 5B, and 5C. The inflatable body 27 could be in the shape of a portion of a frusto-cone to provide local focused adjustment to the proximal cardia. There could be several spacers 26 in the form of inflatable bodies 27 attached by a fluid path as in FIG. 5B or there could be one inflatable body 27 as in FIG. 5C. This may be advantageous depending on where the fixation element 31 is attached to the device, the cardia and esophagus. This inflatable body 27 could be accessed through a self sealing membrane or inflation element 28. The self sealing membrane could be an injection port or it could be a self sealing surface on the inflatable body 27, or the entire inflatable body 27 could be comprised of a self sealing surface. In all descriptions below, the term inflation element can also refer to an injection port or to an area on the inflatable body 27 with a self sealing membrane. The self sealing membrane could also be a self sealing valve such as a slit valve which can be accessed by a blunt needle or tube to allow access to add or remove fluid. FIG. 5A shows an inflation element 28 that is attached to the device and can be accessed by a blunt needle or small tube instrument to add and remove fluid. As fluid is added, the inflatable body 27 inflates in profile to compress the cardia to create a sensation of satiety.

Figure 6A:
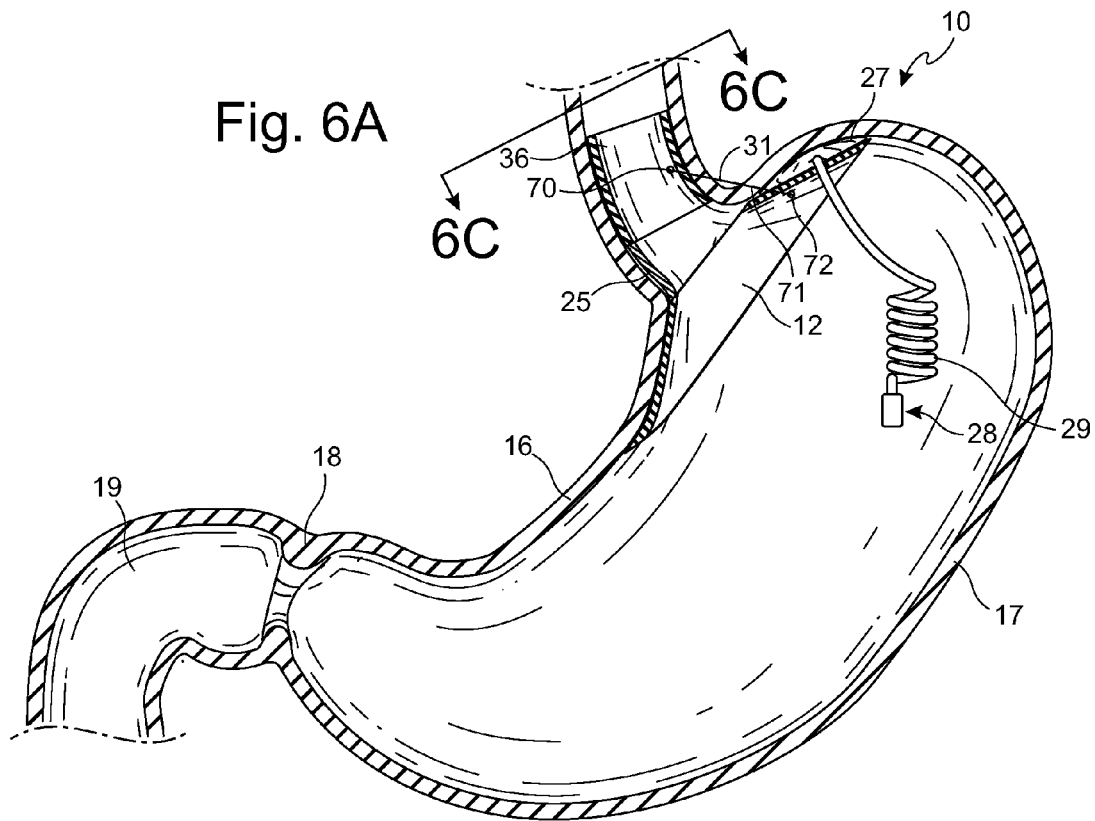
FIG. 6A depicts a side of an embodiment of a bariatric device of the present invention with an adjustment mechanism and a retractable leash located within a cross-section of a stomach.
Figure 6B:
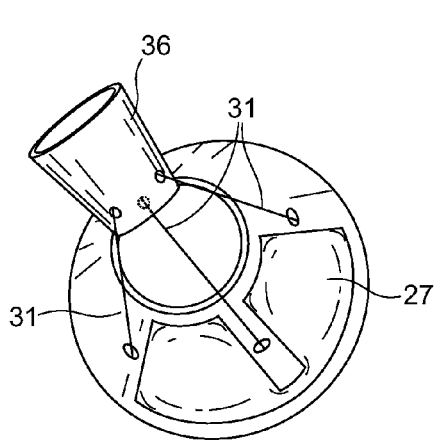
FIG. 6B depicts a top view of an embodiment of a bariatric device of the present invention with an adjustment mechanism.
Figure 6C:
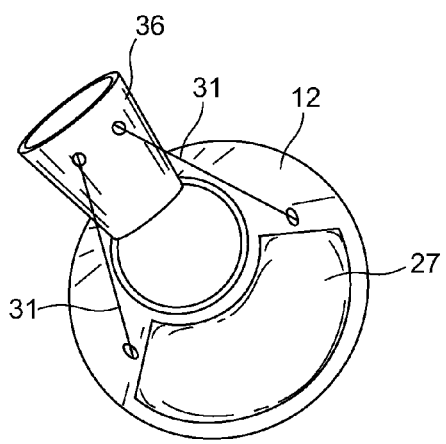
FIG. 6C depicts a top view of an embodiment of a bariatric device of the present invention with an adjustment mechanism.

An alternative would be to have an inflation element 28 that is attached by a length of tubing 29. The tubing 29 could be straight or coiled. FIG. 6 shows a coiled tube or retractable leash 29 with an inflation element 28 or valve attached to the end of the leash. This would allow the leash to be accessed endoscopically by an instrument, and then extracted up the esophagus for access outside the body. Using an instrument, the inflation element 28 or valve could be accessed to add or remove fluid, and then placed back down the esophagus and into the stomach.

Figure 8B:
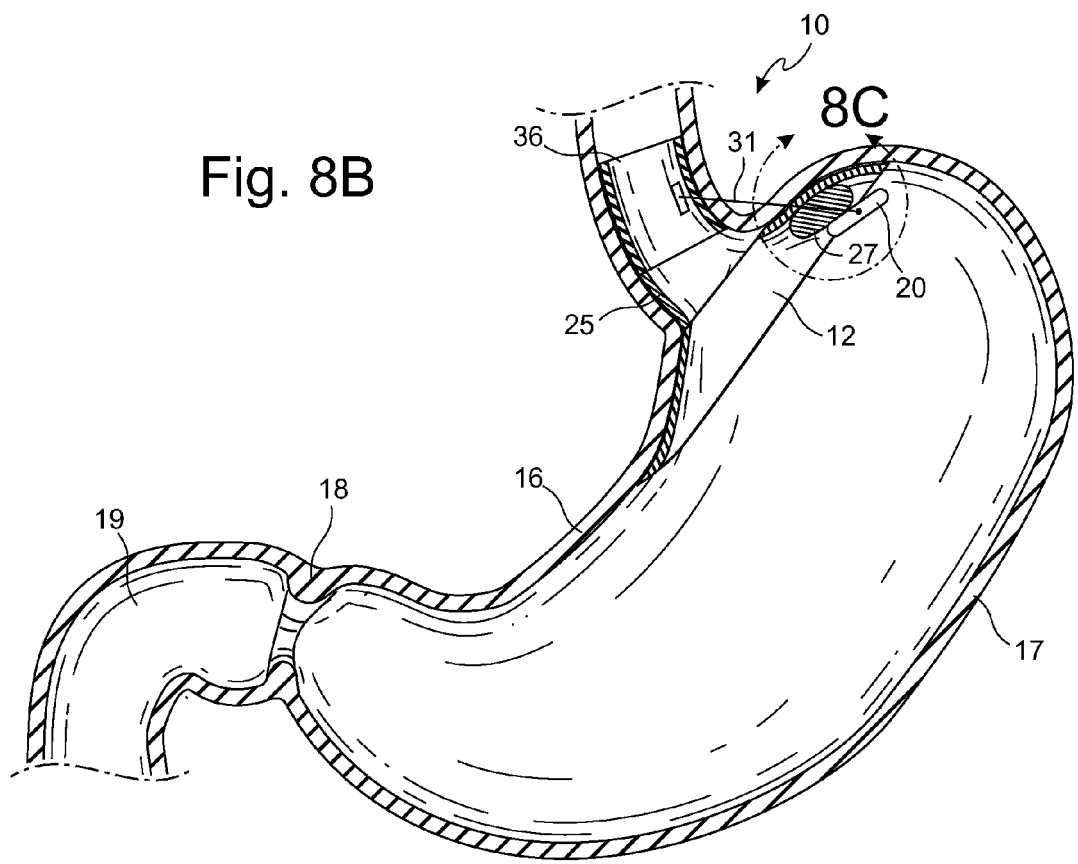
FIG. 8B depicts a side view of an embodiment of a bariatric device of the present invention with an adjustment mechanism located within a cross-section of a stomach.
Figure 8C:
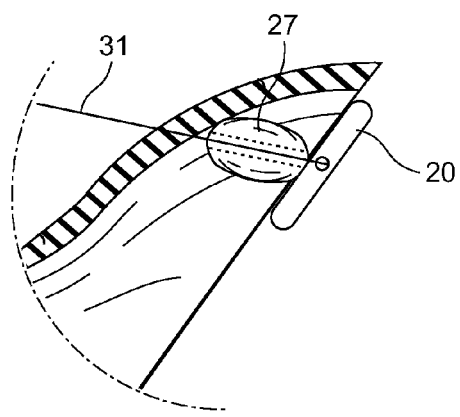
FIG. 8C depict a close up side view of an embodiment of a bariatric device of the present invention with an adjustment mechanism in the adjusted state.

Another embodiment to adjust the length of the fixation element 31 or connecting elements 25 could use spacers. In this embodiment, the fixation element 31 may employ a first anchor 70 with a fixed profile, a connector 71, and a second anchor 72 that can change in profile in the form of a toggling T-bar 20 as shown in FIGS. 7A and 7B. Alternatively, the anchor 72 could be equipped with a collapsible basket 30 that can change profile from long and narrow for pushing through a small opening and changing provide to wide and flat to secure the anchor as shown in FIGS. 7C and 7D. Either the T-bar fixation 20 or the collapsible basket fixation 30 allow the fixation to pass through the esophageal member, esophagus, cardiac member and cardia and then allow then change the profile of an anchor 72 inside the stomach. For example after placement, the T-bar 20 could be grasped and then modular spacers placed above it to adjust the tension placed on the suture and cardia. FIG. 8A shows a spacer 26 above the T-bar 20 connection. Other means of fixation could also be used. The spacer 26 could also be an inflatable body 27 that could expand to act like a spacer to apply more compression to the cardia. This inflatable body 27 could be accessed through an inflation element 28, not shown, to add or remove fluid. See FIGS. 8B and 8C.

Figure 8D:
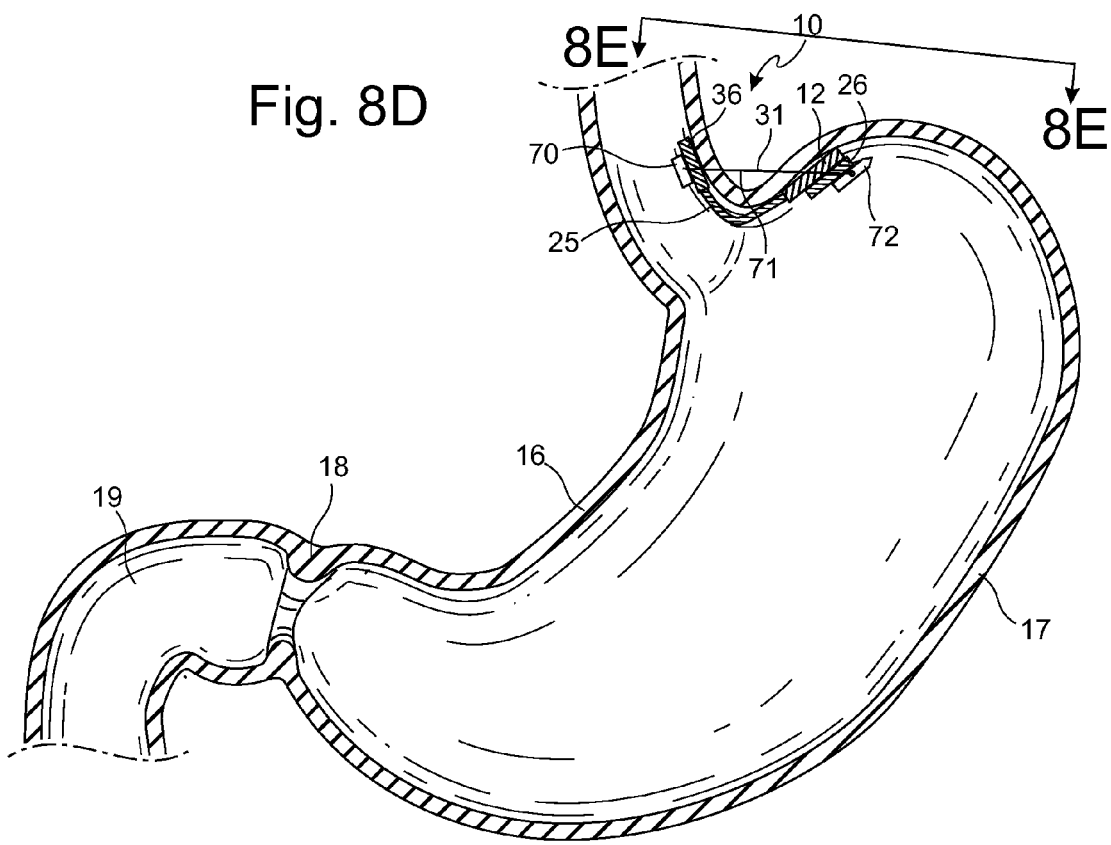
FIG. 8D depicts a side view of an embodiment of a bariatric device of the present invention with an adjustment mechanism located within a cross-section of a stomach.
Figure 8E:
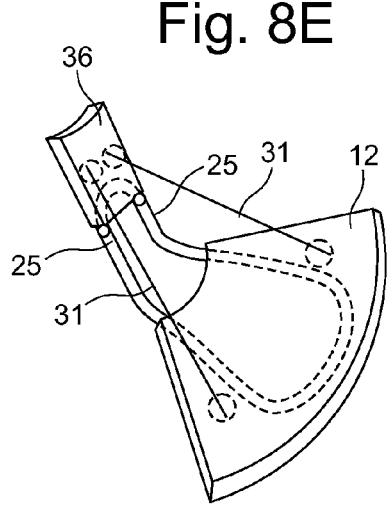
FIG. 8E depicts a perspective view of an embodiment of the bariatric device of the present invention.

Another variation of a 3 element embodiment is shown in FIG. 8D and has elements that contact the lower esophagus and the proximal cardia. FIG. 8D shows a side view of this embodiment and 8E shows an isometric view. The esophageal element 36 that contacts the lower esophagus could be a portion of a steep frusto-cone or tube. The cardiac element 12 could be a portion of a flattened frusto-cone or tube. Although the esophageal and cardiac elements of this embodiment are shown as portions of frusto-cones, the members of these elements could be a variety of different shapes, including substantially planar. One of the features of this embodiment is an esophageal and cardiac elements are non-lumenal, meaning they do not form a lumen. These esophageal and cardiac elements could be constructed of silicone, a combination of silicone and Nitinol, or other suitable materials or combinations of materials. These esophageal and cardiac elements could be connected by a shaped connecting element 25 such as a wire form, strut or could be seamlessly integrated into one piece such as with narrow panel. The portion that connects the esophageal and cardiac members could be formed in a right angle or less (an acute angle) to apply compression to the upper cardia. The portion of the connecting element that passes through the gastroesophogeal junction may be low profile to allow the esophageal sphincter to close. FIG. 8E shows an example of the connecting element 25 as a shape set Nitinol wireform with an angle. Since the wireform is low profile made with small diameter wire, the wires could flex and would allow the GE junction to close during peristalsis. The device would be collapsible so it could be placed down the esophagus and then fixed into place from inside the esophagus for a fully endoscopic procedure. The fixation element 31 could comprise one or more fixation connectors 71 held in place by anchors 70, 72. The anchors 70, 72 could be fixed to the esophageal and cardiac elements 12, 36 alone, or could be fixed to those elements and the esophagus and upper stomach or cardia, or any combination thereof. Then the fixation connector 71 can be passed from inside the esophagus through the esophageal member 36 of the device through the cardia to the cardiac member 12 to fix it in place. See FIG. 8D. More than one point of fixation could be placed to hold the device in place and to apply pressure to the upper stomach.

This device could then contain several types of adjustments. For example, the fixation element 31 that attaches the device in place could comprise an anchor comprising a toggle T-bar 21. This would allow the toggle to pierce through the esophageal member 36, esophagus 32, cardiac member 12 and cardia and then allow the toggle to rotate to create fixation inside the stomach. After placement, the T-bar 21 could be grasped and then a modular spacer or spacers 26 placed above it to adjust the tension placed on the suture and cardia. FIG. 8D shows a spacer 26 above the T-bar 20 connection. Other means of fixation could also be used. The spacer could also be an inflatable member that could expand to act like a spacer to apply more compression to the cardia as shown in similar previous embodiments. This inflatable member could be accessed through an injection site 28 to add or remove fluid.

Another adjustment feature could be to place a spacer 26 in the form of an inflatable member 27 on top of the cardiac element 12 of the device that could be accessed through an inflation element 28. This inflation element 28 could be a self-sealing septum of a port or it could be incorporated into the balloon surface itself. The inflation element 28 could also be a valve, which may include a self-sealing membrane, that can be accessed by a blunt ended needle to allow fluid to be added or removed. As mentioned previously, the inflation element could be connected to the inflation member 27 by a tube and this tube could be straight tubing or coiled tubing 29 to allow the valve to be pulled up the esophagus and accessed outside the body. As fluid is added the balloon inflates in profile to compress the cardia to create a sensation of satiety. Similarly, fluid could be removed to reduce the sensation of fullness. FIGS. 5A, 5B 5C 6A, 6B and 6C,show how a similar balloon could perform on this embodiment.

Another variation of this embodiment would be to allow spacers 26 to be placed into a pocket or feature of the cardiac element 12 to apply outward force for additional pressure against the cardia. The spacers could be made from solid or hollow sections of polymers, silicone or foam. The spacers could also take the form of a shape set self expanding Nitinol feature that could apply pressure to the cardia, but give during peristalsis. These self expanding Nitinol features could have a variety cross-sectional shapes, angles, and resistance to allow for a range of compression to be applied to the cardia. As shown in FIGS. 4A, 4B, 4C, 4D and 4E, the spacer 26 could be self expanding material, shaped like a one sided arch, a hemicone, a hemi-frusto-cone, a generally conical shape or other suitable shapes. The spacer 26 could be removed endoscopically with a collapsing drawstring and then replaced for a different spacer to change the amount of pressure applied to the cardia.

Another embodiment of this device could allow the connecting element 25 to be modular and replaceable with different angles or positions to increase the compression on the esophageal and cardiac elements 36, 12. The esophageal and cardiac members 36, 12 could both be fixed as shown in FIG. 8D, but the connecting element 25 could be modular. The connecting element 25 could comprise a wire, such as a shape set Nitinol wire that could fit inside of a pocket or feature on the esophageal element 36 and also fit into a pocket or feature on the cardiac element. The wire would attach and apply pressure to the cardia based on the shape set angle. If the pressure were not great enough, the connecting element 25 could be removed and replaced with another that had a more acute angle. Similarly, there could be several positional features of pockets to allow a variety of assembly lengths, angles and configurations with the modular connecting element in place. In another variation, the shape set wire could attached directly to the fixation and not require a separate esophageal or cardiac element. Although Fig, 8E shows a connecting element made from a single member, the connecting element could be comprised of several members to allow for ease of modularity or attachment.

The device could also be adjusted by other manual means by using a gastroscopic instrument to come into direct contact with the device, in order to adjust the pressure applied by the cardiac element to the cardia wall.

The instrument could act as a screw driver to rotate a member to thread the two elements closer or farther apart.

The instrument could also act as a pusher or puller to activate a pulley mechanism or a clipping mechanism. For example, the third element could be strut with multiple positional features such as holes, grooves, teeth or wedging. The device could have a feature to engage the ratchet teeth or positional features such as a pin or clip. The instrument could retract the pin or compress the clip and then reposition this feature in the next available location.

The instrument could also deliver heat directly to a heat-expanding mechanism (such as one made of Nitinol) for expansion, or a wax or wax-like expansion member.

For example, the Nitinol clip could clip into a positional location on the strut. The instrument could heat the clip to release and then reposition it into a different location, remove the heat and allow the clip to re-engage the positional feature to lock it into place.

The instrument could also have an inflatable balloon to allow for physical contact with the device to disengage a feature for repositioning into another location.

There could be several other means for manually actuating the design for repositioning.

As another variation of the above embodiments, the manual expansion mechanism could be adjusted remotely by an apparatus outside the body, and/or automated. The expansion could be achieved by a small motor that could be driven by an implanted power source or driven by a remote power source such as induction. Energy could also be supplied by an RF signal, kinetic energy, ultrasound, microwave, cryogenic temperatures, laser, light, or thermal power. Power could also be supplied by a battery or implantable power cells that utilize glucose or other means for fuel.

The automated expansion could also be achieved by a pump, a syringe type plunger, a piezoelectric crystal, a bellows, a Nitinol motor, a pH responsive material that changes shape, thermal expansion of a gas, fluid or solid (example wax) expansion, magnet forces or any other type automated expansion or compression mechanism.

The control for activating this mechanism could be a remote control using a radiofrequency signal which can pass through tissue. The remote control could also be achieved by magnetic fields, time varying magnetic fields, radio waves, temperature variation, external pressure, pressure during swallowing, pH of any frequency or any other type of remote control mechanism.

Actuation Elements

Figure 9A:
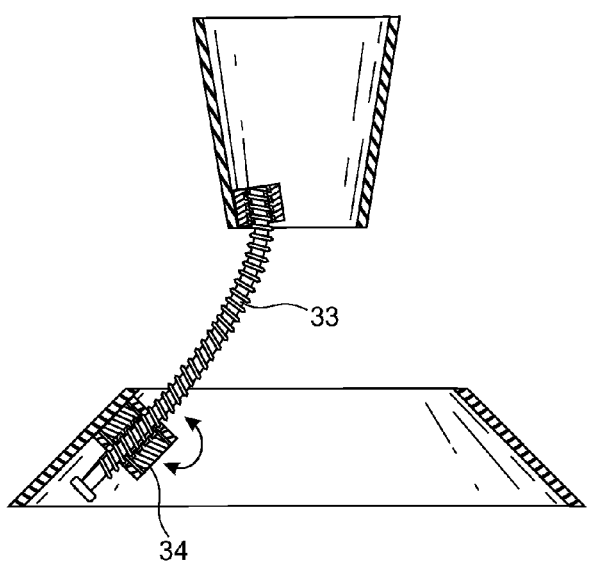
FIG. 9A depicts a side view of the embodiment of a bariatric device of the present invention with an adjustment mechanism.
Figure 9B:
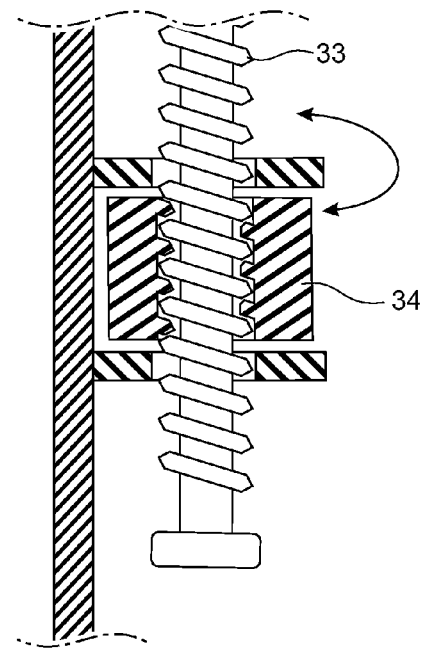
FIG. 9B depicts a close up of the adjustment mechanism of 9A.

Stepper Motor:

To adjust the distance between the cardiac and esophageal elements 12, 25 to increase the direct force onto the upper stomach or cardia, thereby adjusting the pressure applied by the cardiac element to the cardia wall, the adjusting element could modify the length of the fixation or connecting element 31, 25. These elements could be entirely or partially comprised of a flexible, semi-flexible or rigid screw 33. An actuation element, such as a stepper motor 34 could be placed onto the flexible thread and could drive forward or back to allow the fixation and/or connecting element to draw together or push apart the elements. See FIGS. 9A and 9B.

These figures represent a threaded element that can be drawn together or apart. As an alternative, the motor could be modified to contain a lumen to accept a suture or flexible connecting member 71 with a fixation anchor that changes profile 72 or another means of fixation that can pass through a lumen and then expand beyond the lumen for fixation.

The adjusting element may require power to drive the actuation element, in this case the motor. The power could be supplied by an implanted power source such as a battery or it could be powered externally by induction through the coupling of an external antenna and an internal antenna.

An option would be to embed the internal antenna into any or all of the elements. This would allow for fewer structures in the design by encasing the antenna inside of one or more of the existing elements. The antenna could be a simple ring at the top or bottom or obliquely on either element or it could be placed in the wall of the device. The internal antenna could also be attached by a tether, free floating inside the esophagus, stomach or intestine. These could be made from materials to make them MRI compatible and/or MRI safe. This feature could be applied towards any actuation method where it is powered by induction.

Figure 10A:
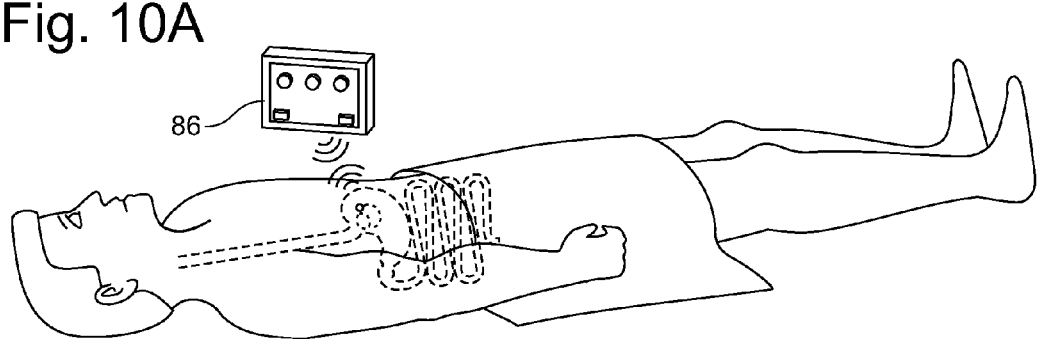
FIG. 10A depicts a remote controller of an embodiment of the present invention, worn next to the user's body.
Figure 10B:
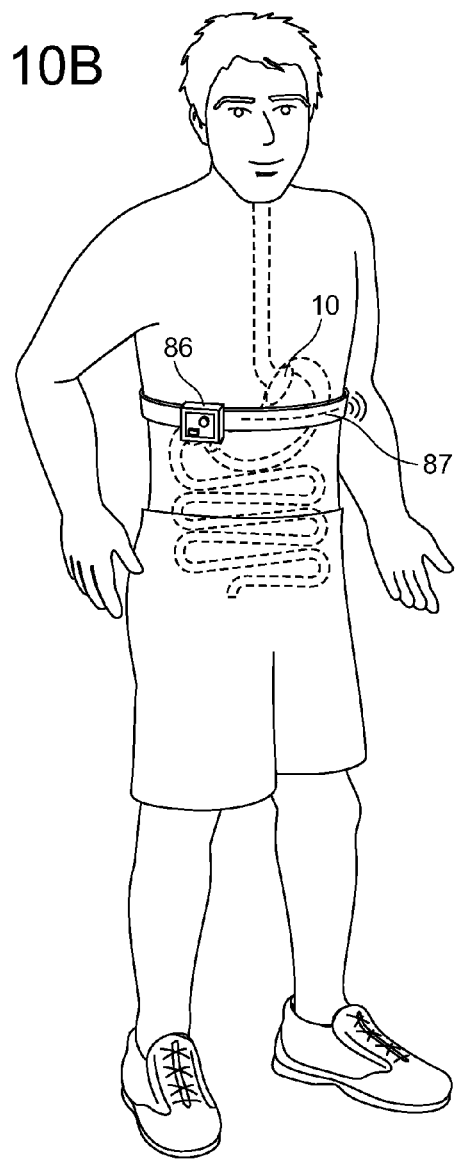
FIG. 10B depicts a remote controller of an embodiment of the present invention, used without wearing or placing adjacent to the body.

For induction, an external hand held controller 86 may be required to transmit power for coupling. See FIGS. 10A and 10B. The controller 86 could be set up to auto detect the internal antenna's presence and identify when coupling between the two antennas was adequate to allow for transmission and powering to take place, and to inform the user of function. This external controller 86 could then be used to display the distance that the stepper motor had been advanced or retracted to allow the physician to control the adjustment. Similarly, the external controller 86 could be used for communication and control signals as an interface between the physician and the placed device. This feature could be applied towards any actuation method powered by induction.

An external antenna would be required for induction and could be placed into an external handheld controller 86. This could be placed directly against or close to the patient's body at the height of the internal bariatric device. See FIG. 10A. The antenna could be housed with the other controller electronics in a single unit. This feature could be applied towards any actuation method powered by induction.

Another alternative would be to have the external antenna in the form of a belt 87 that would wrap around the patients abdomen at the height of the device to better align the antennas for improved coupling. This feature could be applied towards any actuation method powered by induction. See FIG. 10B.

The location of the actuation mechanism could also be inside any of the elements, or above or below any of them, or another location as would be best suited for the anatomy and function of the device. This feature could be applied towards any actuation method. Actuation could be accomplished by allowing the screw to be pushed or pulled inside any of the elements to embed the adjustment mechanism internally to one of the other elements. Other actuations mechanisms such as those listed above or others could also be used for this adjustment.

Induction could also be powered by an intragastric instrument. The instrument could have a flexible shaft that could fit through the mouth and down the esophagus or down the working channel of a gastroscope. Once the instrument was placed within or near the esophagus or stomach, it would allow the instrument to be in close proximity with the actuation mechanism in the device. The end of the instrument could have antenna(e) to allow for inductive powering and/or communication with the actuation mechanism for adjustment. This feature could be applied towards any actuation method.

Piezoelectric Motor

The adjustment for adjusting the pressure applied by the cardiac element to the cardia wall could also be achieved by a piezoelectric element or motor. See FIGS. 9A and 9B. These figures represent a threaded element that can be drawn together or apart. This feature could be applied to the connecting or fixation elements.

There are several types of piezomotors that could be used for linear actuation. For example, a motor from NewScale Technologies (www.newscaletech.com) called the Squiggle Motor could be used which is very low profile and can be actuated when powered. Other motors or actuation mechanisms could also be used, and the Squiggle motor is just used as an example. In this example, there is a rigid screw 33 that passes through the center of a threaded piezoelectric "tube" or element. When powered the piezoelectric element flexes side to side along the central axis to create an oscillating "hula hoop" action which causes it to translate axially along the rigid screw 33. The Squiggle motor could be attached to the esophageal, cardiac, connecting element or fixation elements 36, 12, 25, 31 to advance or retract the cardiac and/or the esophageal elements 36, 12. Alternatively, the Squiggle motor could be placed in between any of the elements. Alternatively, more than one Squiggle motor could be placed at these locations. One of the advantages of a piezoelectric motor is that it would allow the device to be MRI compatible and safe. As mentioned with the stepper motor 34 above, the piezoelectric motor could be powered by an internal power source such as a battery or it could be powered by remote induction. The remote induction could be by a handheld external controller 86 or it could be by a gastroscopic instrument placed down the esophagus. This motor could be encased in other materials to keep it dry and protected from the stomach environment.

Another embodiment of a piezoelectric actuated motor would be to have a rotating piezoelectric member that could thread along one or two threaded members similar to a worm gear.

Another embodiment of a piezoelectric actuated motor would be to have a piezoelectric crystal that elongates or flexes to actuate another member.

All of the piezoelectric motors may contain a sealed housing such as an expandable metal or plastic bellows to prevent moisture of fluid from contacting the piezoelectric elements.

Magnetic Actuation

As mentioned above in the manual adjustment section, another adjustment mechanism for adjusting the pressure applied by the cardiac element to the cardia wall could use magnets.

Figure 9C:
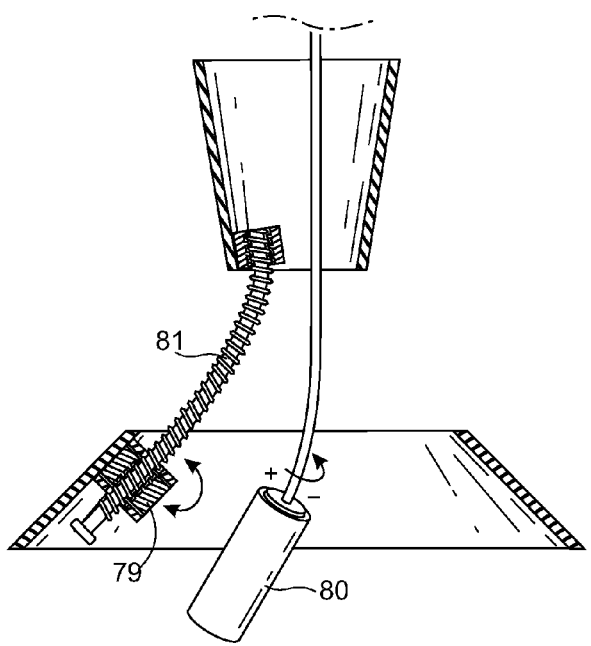
FIG. 9C depicts a side view of the embodiment of a bariatric device of the present invention with an adjustment mechanism.
Figure 9D:
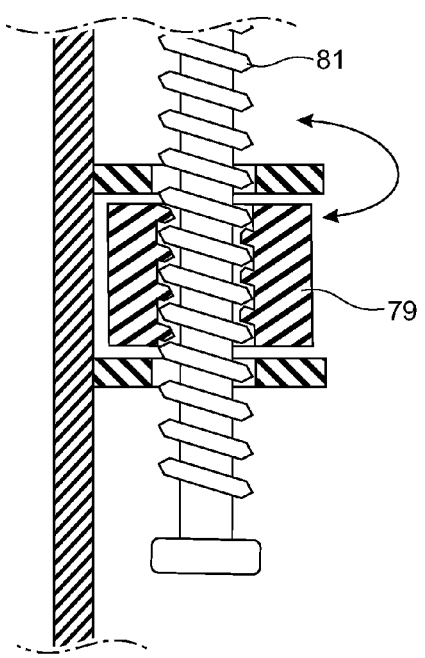
FIG. 9D depicts a close up of the adjustment mechanism of 9A.

For example, at least a portion of the connecting or fixation element 25, 31 could be a semi-flexible thread or rigid threaded member 81 with a magnetic nut 79 placed over it. Another strong magnet, named a controller magnet 80, could be placed in close proximity to the implanted magnet nut 79 to cause it to rotate. The rotation of the controller magnet could create a magnetic field which would cause the internal magnet to turn allowing it to advance and retract along the threaded member. See FIGS. 9C and 9D.

The controller magnet 80 could either be external to the body or it could be placed on the end of a gastroscopic instrument for close proximity.

The controller magnet 80 could be a magnet or an electromagnet to increase the intensity of the field and to improve magnetic coupling to ensure actuation.

The controller magnet 80 could also be multiple magnets to improve magnetic coupling.

Nitinol Actuation

The adjustment element could also be actuated by Nitinol or a substance with similar properties. When a current is passed through Nitinol, it heats and causes the Nitinol to change its shape. Nitinol can expand into a variety of different shapes. A linear actuator could be made from Nitinol to advance or retract along an actuation member.

Heat could be generated from an implanted battery or it could be delivered by induction.

The cardiac, esophageal, connecting or fixation 12, 36, 25, 31 element could have multiple positional features such as holes, grooves, teeth or a wedging feature. A Nitinol clip could have a feature to engage these positional features. The Nitinol clip could be heated to change shape to allow it to advance or retract into different positional features to increase or decrease the length.

There are other Nitinol actuations that could be provided as well.

Ultrasound Motor

Another adjustment mechanism could be by use of an ultrasound motor or one powered by external ultrasound. This could use external ultrasound equipment to send sonic waves into the body to actuate the motor. This would also provide an MRI compatible option without requiring an internal power source or induction.

Hydraulic Actuation

The adjustment element could also be actuated through hydraulic means for radial expansion, linear actuation, shape change or stiffness change as previously described. The cardiac or esophageal element 12, 36 could be inflated with a fluid to increase the profile, diameter or length of the device to increase pressures against the upper stomach or cardia. It could increase in volume by accessing a self sealing membrane such as a self sealing drug delivery port, self sealing membrane on the expandable body, or a self sealing valve attached to the device. The inflation could be achieved by a piezoelectric pump, a peristaltic pump, a positive displacement pump or a syringe pump.

Piezoelectric pump: The pump could be comprised of a piezoelectric element which can flex to propel fluid directly or a member that could propel fluid. For example, a piezoelectric disk could be captured in a housing with an incoming channel and an outgoing channel. The disk could be powered to cause it to flex into a dome shape to push fluid into the outgoing channel. A valve would be required to close the incoming channel to ensure directional flow to the outgoing channel. Similarly, the piezoelectric Squiggle motor as described above could be used to linearly actuate a fluid up or down a tube to hydraulically actuate position.

Stepper motor pump: Actuation could be achieved by a stepper motor where the motor linearly actuates to compress a reservoir or syringe to move fluid within a tube or constrained volume.

Wax expansion pump: Fluid could also be propelled by a wax expansion mechanism. When wax is heated to melting it expands by approximately 30%. A solid plug of wax could be heated to expand and drive fluid through a valve to hydraulically actuate lengthening. The lengthening structure could be made to move only in one direction, so that when the wax cools it will not contract. The wax expansion could also be used to actuate other adjustment mechanisms.

Peristaltic pump: The members could also be driven by a peristaltic pump. In this mechanism, the external diameter of a cylindrical actuator could be used to compress a length of tubing to create an occlusion. The cylindrical actuator could be rotated along the tube to drive fluid forward or backwards inside the tube. The peristaltic pump could also be actuated by a stepper motor or by a piezoelectric element or other.

Gas expansion/propellant pump: The length could also be actuated by a gas expansion pump where a gas like Freon or others could be used to expand when exposed to a higher temperature. Similar principles to the devices like the Codman pump could be used. This change in volume could drive the pump forward. Similarly, there could be compressed gas constrained in a pressure vessel with a valve. The valve could be remotely activated to allow gas to propel a syringe, fluid or to compress a constrained volume.

Positive displacement pump: There are implant grade positive displacement pumps that are available on the market for drug delivery that could be used to displace a specific amount of fluid for hydraulic inflation of the adjustment element.

Syringe pump: A syringe pump could be made by advancing fluid through a syringe. The syringe could be actuated by a stepper motor, a piezoelectric actuator, a magnet or by a Nitinol actuator as described above.

Hydrogel: the adjustment element could also be inflated by use of a hydrogel to absorb fluids and could be actuated by changes in temperature, pH or tonicity to change shape or volume Hypertonic fluid: the adjustment element could also be inflated by using a hypertonic fluid in the inflation area and allowing it to absorb fluid across a semi permeable membrane.

Mechanical means for diametrical or profile changes. Similar to the inflation, elongation, and shortening embodiments described above, the device could change diameter by various actuation mechanisms. All of the above-described mechanisms could also be adapted for use for a diametric change instead of a linear change.

As a variation of the embodiments discussed above, the device could have a sensor that could sense a parameter such as pressure, motion, peristalsis, tension, pH, temperature, chemical or other appropriate parameters, or various parameter combinations. The sensor could output a signal to be used by an actuation element to actuate an adjustment element, to a memory element such as a microchip, or be read by a remote reader or remote controller.

Figure 11A:
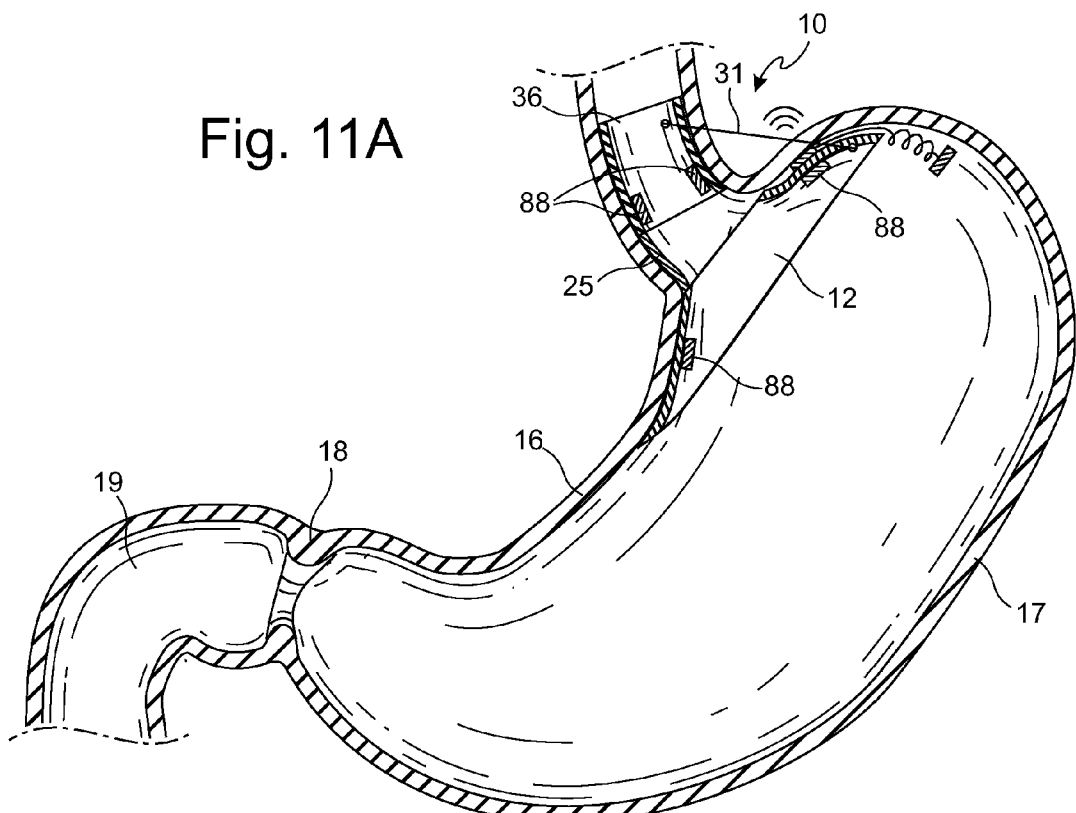
FIG. 11A depicts a side view of an embodiment of a bariatric device of the present invention, located within a cross-section of a stomach.
Figure 11B:
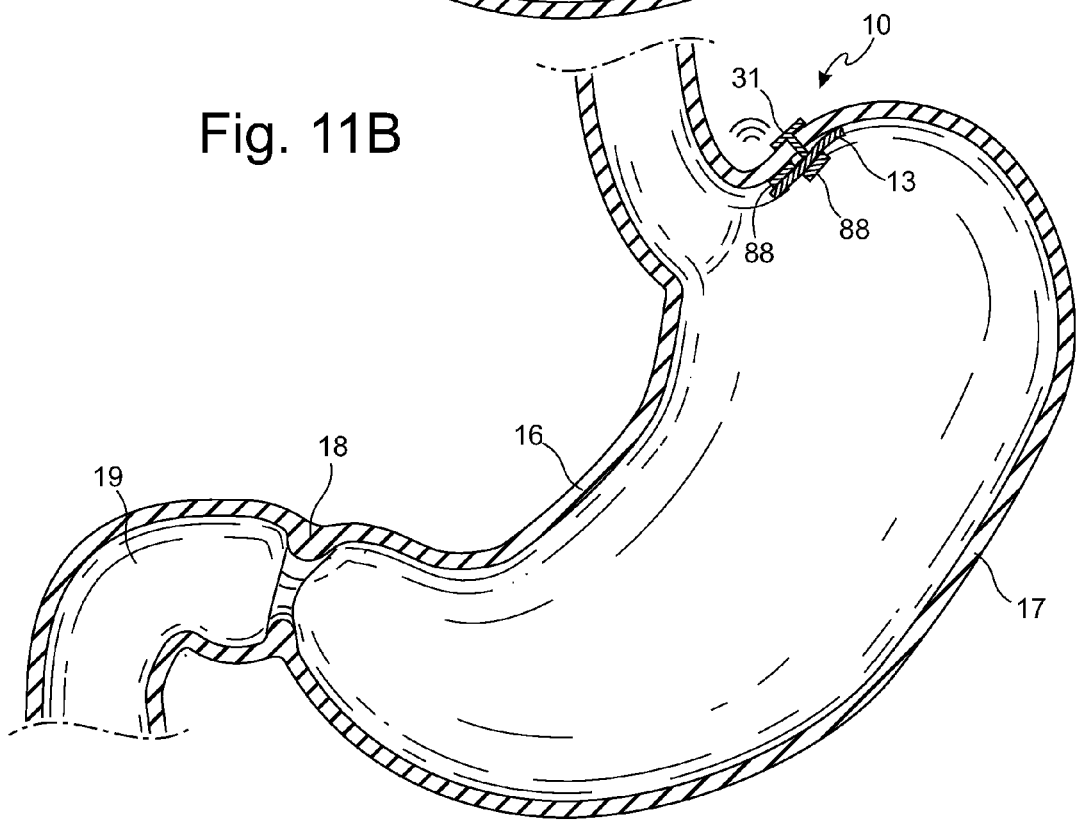
FIG. 11B depicts a side view of an embodiment of a bariatric device of the present invention, located within a cross-section of a stomach.

Sensors 88 could be used to gather important patient data to understand fit, performance, patient status, whether an adjustment needs to be performed, and as a guide while an adjustment is performed. For ease of use and compatibility with the body, wireless sensors would be preferred. In some applications, it may be desirable to sense a parameter without the need for adjustability. In other applications, adjustability for adjusting the pressure applied by the cardiac element to the cardia wall may be a desirable feature. The sensors 88 could be in direct tissue contact, intermittent tissue contact or could monitor the intraluminal pressure inside GI tract. The data could be used for no other reason than to just monitor patient status and performance. FIGS. 11A and 11B depict sensors 88, which could be embedded in any of the element surfaces for direct tissue contact, non-tissue contact or it could be tethered to any of the elements to allow it to be suspended inside the GI tract. Based on the sensed parameter, the device could be adjusted. The adjustment could have an open or closed loop system increasing or decreasing the applied force, pressure or sensed parameter. The sensed parameter could detect whether the device was not at an ideal condition, and could then send a signal to a control mechanism for automatically adjusting the system. This mechanism could be under physician control (open system) or without physician control (closed system). The adjustment could also be a manual adjustment where the parameters are being monitored to guide the adjustment. It could also control the shape of the cardiac, esophageal, connecting, and/or fixation elements 12, 36, 25, 31 to vary stiffness, size, length, form or shape. In general, the sensor 88 could sense a parameter and then adjust the device as needed to bring the sensed parameter into the ideal range. There could be an algorithm that controls the ideal parameter or it could be based on a parameter range. The device would be adjustable to meet the needs of the patient.

In an open loop system, the physician would have control of when the device would adjust the pressure applied by the cardiac element to the cardia wall. The device could have its own internal power source, or it could be passive and only inductively powered when in close proximity to an external controller 86 under the supervision of a physician. For example, in the clinic the physician could have a remote controller 86 with the ability of powering the device inductively, and then begin to monitor the sensors 88 feedback signals to see physical parameters of the patient at baseline such as pressure of the device against the cardia. The sensor monitoring could also be performed while the patient is eating or drinking, or not eating or drinking As the patient consumes, the esophageal and stomach peristaltic waves will increase in intensity as they propel the food or drink from the mouth to the stomach. A sensor 88 could detect when these waves increase in amplitude, frequency, and pressure. The parameter could read on the external controller by the physician, and then the physician could send a signal to the automated expansion mechanism in the device to adjust the device. The physician could then query the sensor 88 again to determine whether the device was in the ideal settings and whether the pressure against the cardia or sensed parameter was optimized. The physician could iteratively control the amount of adjustment and monitor the parameters until the ideal condition was met. Where the device has its own power source, the physician would still have the control to wake up the device, query the sensors and then adjust the device as described above. The only difference would be that the device was powered by the power source and not require inductive power from outside.

Alternatively, the physician could read the parameter signals while under his supervision, but have the sensors 88 send a signal directly to the automated expansion mechanism to adjust the pressure applied by the cardiac element to the cardia wall until the device was within the ideal parameters. The data collected could be analyzed by the controller for averages, minimums, maximums and standard deviations over time and use an algorithm to determine the ideal settings. The controller could then monitor and adjust on its own until the ideal conditions were met, but while the physician was present to verify all conditions and verify patient acceptance.

In a closed loop system, the device would be active with its own integrated power source. The device could wake up at routine intervals to monitor or could monitor all the time. The data collected could be analyzed for averages, minimums, maximums and standard deviations over time and use an algorithm to determine the ideal settings. As the patient begins to consume food or drink, the device sensors would detect the sensed parameter and signal the automated expansion/contraction mechanism to adjust the device as needed. In this embodiment, the device could be fully automated and would not require intervention from an outside individual.

In either the open or closed loop system, there could be multiple sensors 88 on the device to determine the pressure or force areas, or other sensed parameters on the device and where it needs to be varied to meet the ideal conditions for the stomach. In the case where the fixation and/or connecting 31, 25 element has multiple members, this could be used to align the device in the stomach to provide a custom fit and response for each person. There could also be a mechanism to adjust the alignment of the cardiac and/or esophageal elements 12, 36 relative to the connecting and/or fixation elements 25, 31. The sensor(s) 88 could have a built in power source or it could have a remote power source such as induction so that it would only wake up and activate when an external controller was brought near.

The device could have integrated memory to allow storage of patient and device data. This could include but is not limited to the serial number, the patient's information such as name, patient number, height, weight; the physician's name, the adjustment history including the date and time, the amount adjustment and the sensed parameters. For the active device, there could be 24 hour data recording of key parameters or there could be data collected at key intervals throughout the day to detect when the patient is eating and whether they are being compliant with their eating. It could record weight tracking, BMI or other data as needed which could be queried by an external controller. This data could also be downloaded into a physician's patient tracking database for ease of patient tracking Similarly, this data could be downloaded and tracked on an internet tracking website, where the patient could log on and see their history and progress. The patient could add information to the website such as weight or an eating log, adverse events or other conditions that the physician or patient would like to track.

In the open system, the physician could choose to collect and record data as needed at the time of the adjustment such as weight, date, time, and adjustment amount or other.

For an open loop system, the device could be adapted to allow for remote adjustments over the phone. This would be especially advantageous for patients living in rural areas where they are far from their physician's office. It could also be for convenience of having an adjustment without having to travel to the physician's office. This would allow a physician to discuss the patient's progress with the patient directly and then query the device sensor to see how the device performance is. Based on the feedback of the device, the physician could then adjust the patient.

In yet another embodiment, the device could have an emitter element for dispensing a drug, hormone or bioactive agent to further induce satiety, weight management or other disease management such as diabetes. The drug could be a weight management drug currently on the market or one to be developed. Similarly, it could be a satiety hormone or other bioactive agent. In the published literature, there is a growing mass of information on satiety hormones. The bioactive agent could be applied by the emitter element through a drug eluting coating, a reservoir with a pump, or a permeable membrane placed on the device where the drugs could pass from the device into the gut. The emitter element could release such substances in response to a signal from a sensor, a timed basis, or other release criteria. The device could have a tube that trails into the intestines to allow the drug to be delivered downstream where the pH is higher and would not destroy the bioactive agent.

The device could have a surface finish or macrotexture for gripping the stomach. If the device could grip the inner mucosa of the stomach or esophagus, it could elongate or expand to further stretch the stomach or esophagus in key areas to induce further satiety as needed. For example, the cardiac element could be a conical spiral or other shape with a surface texture that lightly grips the mucosa and or stomach musculature. If the spiral were made of Nitinol or other temperature-sensitive substance, the device could expand the spiral by a variation of temperature. By applying a temperature variation, such as by drinking a hot liquid or otherwise, the device could expand and cause a satiety response. The surface could be multiple protuberances, barbs, a rough bead blast, or other finishes suitable for gripping the stomach wall.

As a variation of the device, it could incorporate electrical stimulation to the stomach musculature, stomach nerves or the vagus to further improve satiety stimulation and weight loss. Energy used for this stimulation could be RF, ultrasound, microwave cryogenic, laser, light, electrical, mechanical or thermal. The device could have leads incorporated that could embed into the stomach wall or be surgically placed around a nerve, or the stimulation could be applied directly through surface contact of the device to the stomach mucosa.

Single Cardiac Member:

Another embodiment has a single cardiac member that is fixed to the cardia or other region of the stomach with an anchor and applies pressure to the cardia or upper stomach. All of the improvements described above including adjustability mechanisms, manual adjustability, remote adjustability, sensors, data collection, memory, and others may be applied to such devices.

For example, some bariatric devices have a member with a flat button anchor 70 with a T-bar 20 attachment into the cardia. In such a device, an adjustment feature may be applied to increase or decrease the amount of compression applied to the cardia. As mentioned above, several adjustment mechanisms for adjusting the pressure applied by the single cardiac member to the cardia wall could be used such as a stepper motor, a piezoelectric crystal element, hydraulic adjustments, gas or solid expansion, variable tension springs, Nitinol actuation, or any other adjustment noted above. Similarly, the device could be adjusted to change shape such as to increase the surface contact to the cardia or it could change the stiffness to increase resistance. All of these embodiments can be placed and removed endoscopically with a gastroscope and instruments down the esophagus.

Figure 12:
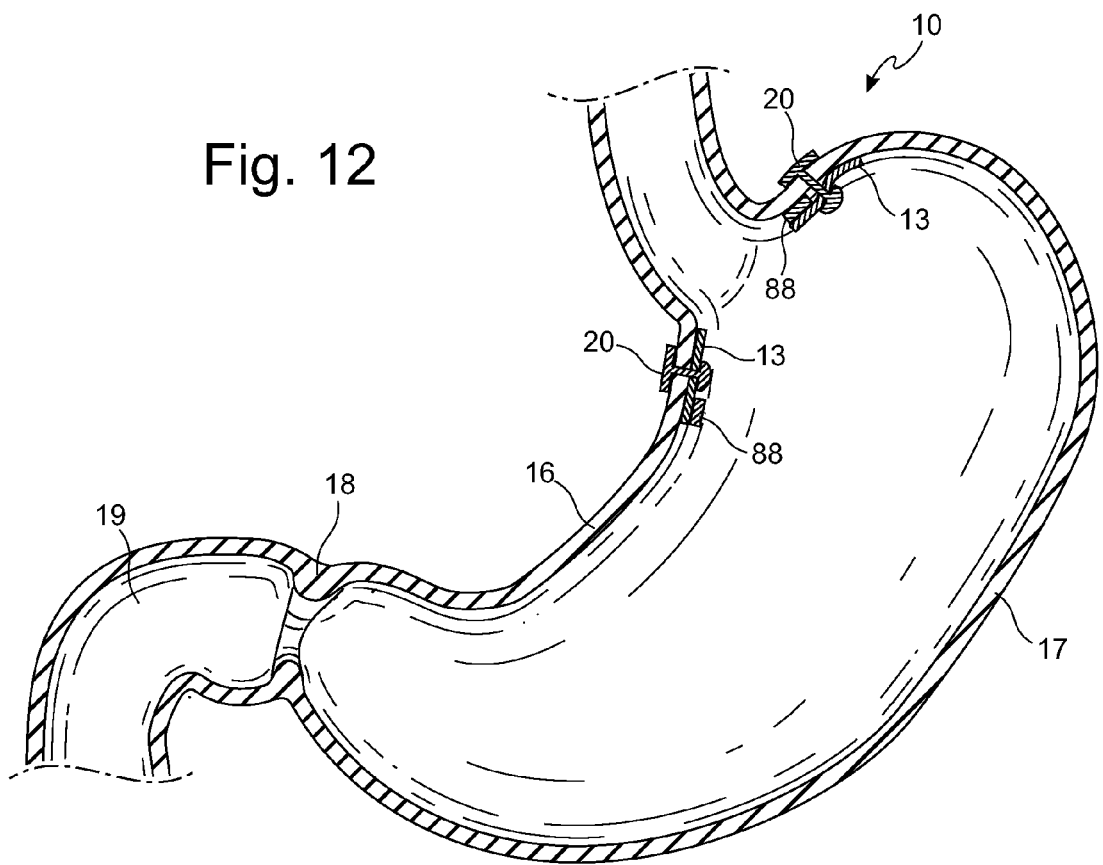
FIG. 12 depicts a side view of an embodiment of a bariatric device of the present invention, located within a cross-section of a stomach.

FIG. 12 shows an embodiment of a single cardiac 13 member where one or more of these single cardiac 13 members could be fixed into the cardia directly at the site where pressure is to be applied. In this embodiment, there is a button anchor 70 with a connecting element 71 that pierces through the cardia with a T-bar 20 which then toggles flat to hold it in place. It also contains a flexible disk or distribution element 61 to distribute the load across a greater surface area than just the button. This also shows sensors 88 that could be located so they contact the patient's tissue or could be located on the outside of the device to monitor the intraluminal pressure. This could be used for monitoring the patient's baseline data, or gathering a variety of other data.

Figure 13A:
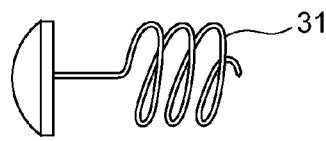
FIG. 13A depicts a side view of a fixation element.
Figure 13B:
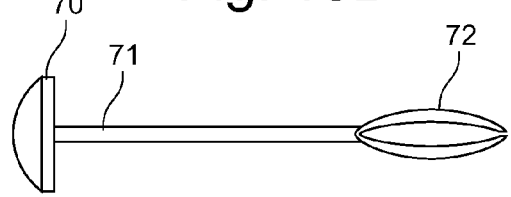
FIG. 13B depicts a side view of a fixation element in the undeployed state.
Figure 13C:
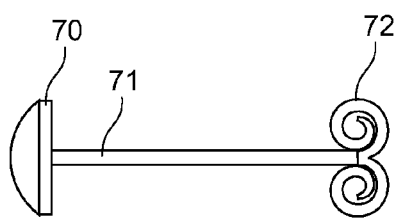
FIG. 13C depicts a side view of a fixation element in the deployed state.
Figure 13D:
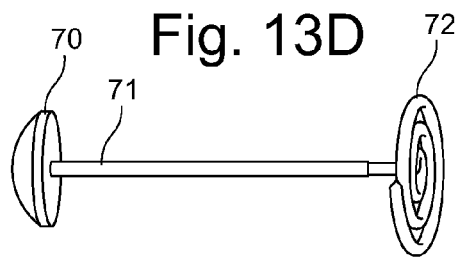
FIG. 13D depicts a side view of a fixation element in the deployed state.
Figure 13E:
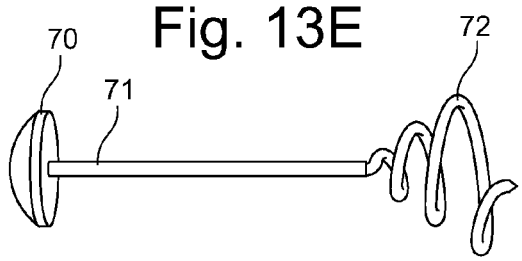
FIG. 13E depicts a side view of a fixation element in the undeployed state.

FIGS. 13A, 13B, 13C, 13D and 13C show several options of fixation elements 31 for fixing the single cardiac member 13 to the cardia. 13A shows a corkscrew or tacker type fixation which would allow the device to be threaded into the place. FIG. 13B shows an elongated anchor 72 with multiple arms that are elongated and collapsed for placement, and 13B shows the same device in its deployed state where the anchor 72 arms curl or spring into a wide, atraumatic profile. The arms are made of shape memory or super elastic material or spring material that changes shape once an elongation force is removed from the device. For example, the device may be placed into a sleeve that holds the curled arms straight. As the arms are advanced out of the sleeve, they puncture through the tissue and then change shape to hold the device in place. In a variation, FIGS. 13D and 13E show another anchor 72 that has shape memory or super elastic qualities where the deployed fixation element 72 shown in a flat spiral shape in 13D, can be completely straightened by placing it into a sleeve and then advancing it until it pierces through the cardia and then springs back into the shape of 13D. FIG. 13E shows the same fixation element with a slightly elongated shape 51 to allow it to pierce the cardia and then spring back into the shape in FIG. 13D. These are examples of fixation elements, and other mechanisms could be used for fixation.

Figure 13F:
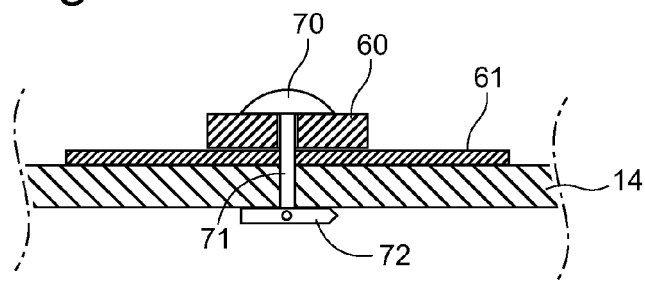
FIG. 13F depicts a side view of an embodiment of a bariatric device of the present invention with an adjustment mechanism.
Figure 13G:
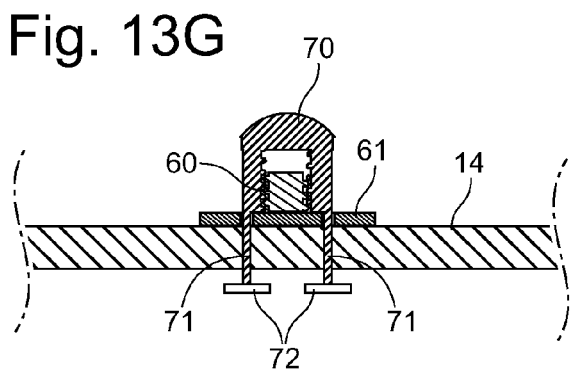
FIG. 13G depicts a side view of an embodiment of a bariatric device of the present invention with an adjustment mechanism.

FIGS. 13F and 13G show an adjustment element 60 that could be used for adjusting the length of the member across the cardia to control the amount of compression applied to the cardia, to adjust the pressure applied by the single cardiac member to the cardia wall. This embodiment shows a distribution element 61 to distribute load across a larger area. This distribution element 61 could be a flat, flexible disk or it could also be a conical shape, spherical, or other shape to improve load distribution or distribution profile across the area. The distribution element 61 could be of a variety of materials which are very soft to firm such as silicone, polymers, foams, Nitinol or it could be a combination of any or other suitable materials. This element could have a single central shaft or connecting element 71 as shown in FIG. 13F or it could have 2 connecting elements 71 that anchor the device for rotational stability as shown in FIG. 13G. The adjustment element 60 could rotate around a central shaft or it could rotate between the 2 shafts. Similarly, the element could have a plurality of shafts for fixing to the cardia.

Figure 14A:
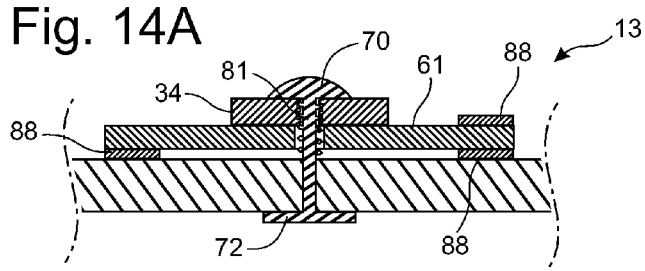
FIG. 14A depicts a side view of an embodiment of a bariatric device of the present invention with an adjustment mechanism.
Figure 14B:
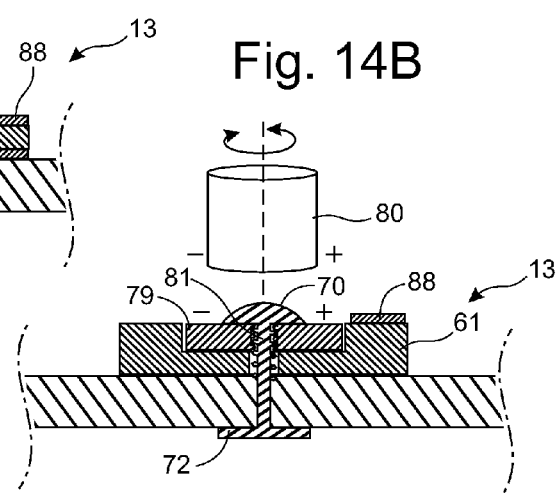
FIG. 14B depicts a side view of an embodiment of a bariatric device of the present invention with an adjustment mechanism.
Figure 14C:
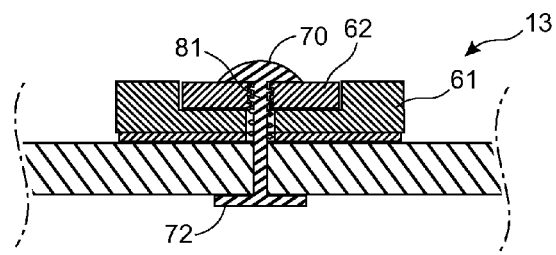
FIG. 14C depicts a side view of an embodiment of a bariatric device of the present invention with an adjustment mechanism.
Figure 15A:
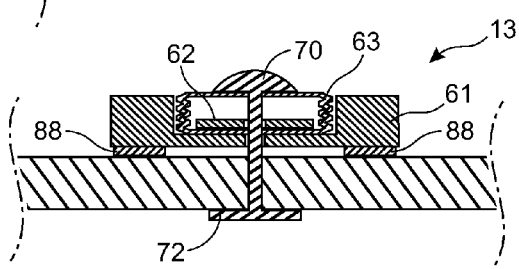
FIG. 15A depicts a side view of an embodiment of a bariatric device of the present invention with an adjustment mechanism.
Figure 15B:
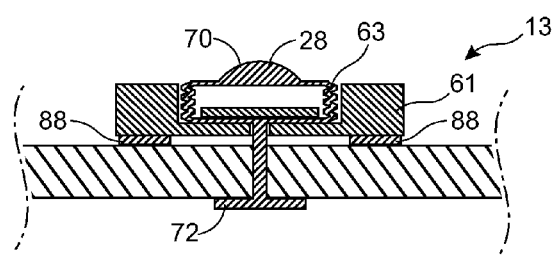
FIG. 15B depicts a side view of an embodiment of a bariatric device of the present invention with an adjustment mechanism.
Figure 15C:
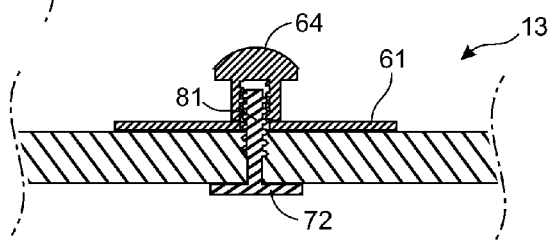
FIG. 15C depicts a side view of an embodiment of a bariatric device of the present invention with an adjustment mechanism.

FIGS. 14A, 14B, and 14C depict 3 different embodiments for actuating a single cardiac member 13. Although the fixation anchor 70 is shown in the drawing as a button, the anchor could also be flat, conical, spherical or other shape. Several adjustment elements could be used for adjusting the pressure applied by the single cardiac member to the cardia wall. FIG. 14A shows a stepper motor 34 that is inductively powered and controlled. The stepper motor could then thread up and down the central shaft to compress the cardia tissue as needed. A sensor 88 could be applied to this embodiment. Optional locations for a sensor 88 are shown. As mentioned above, these embodiments could have 2 or more shafts. FIG. 14B shows a magnetic actuation for adjustment. In this embodiment, there could be a threaded magnetic element 79 that could be rotated by placing a controller magnet 80 in close proximity. As the controller magnet 80 is rotated, its magnetic field causes the magnetic element 79 to rotate. As mentioned above, the controller magnet 80 could be an electromagnet to increase the magnetic coupling or it could include multiple magnets. FIG. 14C shows a piezoelectric element 62, where a piezoelectric element is able to oscillate and rotate to increase or decrease compression against the cardia. A piezoelectric element 62 could also be designed to flex to move the adjustment to different positional locations. FIG. 15A shows another piezoelectric element 62. In this embodiment, the piezoelectric motor 62 is encased in a metal or sealed bellows 63 to seal the element from moisture, if needed. For all the embodiments, they may need to be encased in an acid-resistant and/or moisture resistant barrier. FIG. 15B shows a hydraulic and manual actuation mechanism. In this embodiment, the cardiac member has a self sealing membrane or inflation element 28 that connects to an inflatable balloon. By using a non-coring Huber tipped needle, the needle could be placed down the esophagus and pierce the self sealing membrane to inject or remove saline to expand or contract the balloon to alter the compression. The inflation element could also contain a self sealing valve. In FIG. 15C, another manual adjustment mechanism is shown where the threaded button 64 can be accessed by a screwdriver and rotated along the threaded member 81. This would allow the button to be moved up and down to increase or decrease compression against the cardia. Any type of tool and screw or bolt head feature could be incorporated into the threaded button 64, including Torx, Phillips, polygonal sockets or external bolt heads, or other suitable bolt or screw heads. Gripping feature such as macrotexture could be added to the cardia contacting surface of the fixation element 31 to grip the cardia to prevent it rotating while 64 was being rotated.

A sensor could be placed on the surface of on any element of the device to contact the patient's tissue, or not placed to contact the patient's tissue to gather intraluminal pressure of the stomach, esophagus or intestinal tract, or placed to contact the tissue intermittently. The form of the device could be a single button attached to the cardia or it could be a device with a wall or coil that shapes a cone.

Figure 16A:
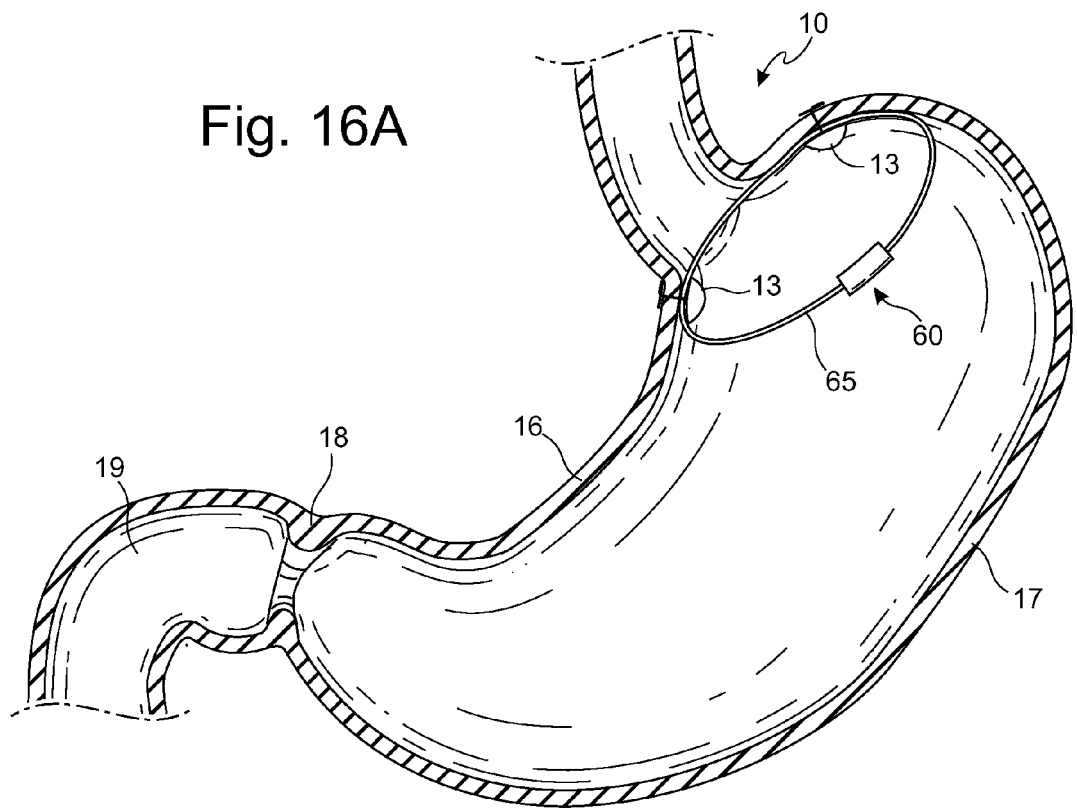
FIG. 16A depicts a side view of an embodiment of a bariatric device of the present invention with an adjustment mechanism, located within a cross-section of a stomach
Figure 16B:
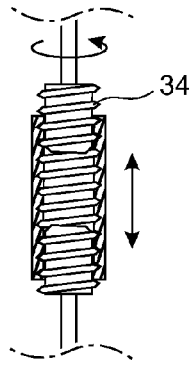
FIG. 16B depicts a variation of the adjustment mechanism in FIG. 16A.
Figure 16C:
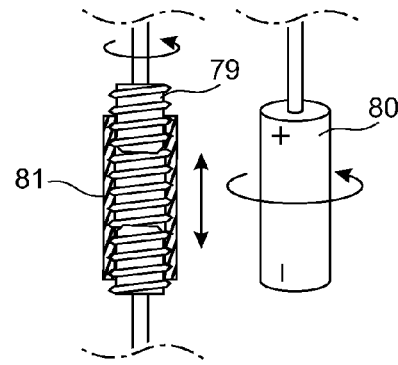
FIG. 16C depicts a variation of the adjustment mechanism in FIG. 16A.
Figure 16D:
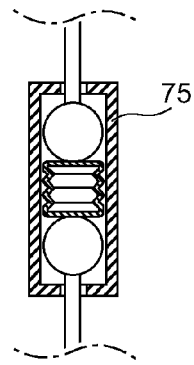
FIG. 16D depicts a variation of the adjustment mechanism in FIG. 16A.

Another alternative would be to connect several single cardiac members with another element such as a loop, band or balloon. See FIG. 16A. In this case, the loop or single cardiac connecting element 65 could be adjusted in length to create a force against the single cardiac member 13 to increase tension against the device, thereby adjusting the pressure applied by the single cardiac member to the cardia wall. The length of the loop could contain an adjustment element 60 which could be expanded to create a greater stretch to engage the stretch receptors. The length of the loop could also be reduced to engage the stretch receptors. The element could pass through a hole or engage a feature in each of the single cardiac members 13. The length of the loop could be adjusted by all of the various methods already described in this invention such as using a stepper motor, magnetic actuation, a piezoelectric element, hydraulic adjustments, gas or solid expansion, variable tension springs, Nitinol actuation, or any other adjustment noted above. FIGS. 16A, 16B, and 16C shows options for adjustability such as use of a motor 34, magnetic actuation of a magnetic nut 79 by a controller magnet 80 or an expansion joint 75 using inflation by a linearly expanding balloon, but other options for adjustability may be used.

FIGS. 17A, 17B, and 17C show an embodiment of a cardiac button 82 which comprises a plurality of penetration prongs 83 which are preferably claw like structures with two ends, hingeably coupled at one end with a coupling element 84 in a generally radial pattern. The generally radial pattern could also vary from true radial, such as 2 sets of parallel prongs at the corners of a square. The penetration prongs 83 could have a long narrow profile, and could be straight, curved, or have a hook or curl at the free end. When the penetration prongs 83 are in an expanded state, their free ends may extend beyond the diameter of their connection point to the cardiac button 82, giving them a splayed appearance as in FIG. 17B. When in a compressed state the free ends of the penetration prongs 83 may approach each other and may even touch, as shown in FIG. 17C. The penetration prongs 83 could be made of a material with spring or super elastic properties to allow them to compress, or a spring mechanism may be incorporated into the cardiac button 82. The penetration prongs may be compressed into the closed state for placement into the cardiac tissue, and then expand into the deployed open state. This would allow for distension of the cardiac tissue. In another embodiment, the penetration prongs 83 could be constructed so that they are in the expanded open state for placement and then collapse to the deployed closed state after placement. This would allow for compression of the cardia tissue. When the embodiment is in the compressed closed state, it can pierce through the cardia for placement and then take the deployed expanded state open to cause the cardia to stretch to engage the stretch receptors and cause satiety. FIG. 17D shows where the element in the expanded open state has penetration prongs 83 that curl into an atraumatic profile. Similarly this device could work in compression where the device is placed in the expanded open state and then closes to compress the tissue engage the stretch receptors. This embodiment could be further improved by having adjustability such as any of the adjustability features already mentioned above. An alternative to this embodiment would be to make the device that changes shape when exposed to a temperature or other stimuli change. This device could further contract or expand when exposed to a hot or cold liquid or stimuli to allow for a temporary adjustment. The adjustability mechanisms described above, including adjustability, remote adjustability, sensors, data collection, surface texture and adjustments over the phone, may be applied to such devices.

Another embodiment would be to have a single cardiac member 13 which only contacts the proximal cardia and is fixed in place with a fixation element 31. This device may have the shape of a portion of a frusto-cone or tube and is fixed in place at each of the 4 corners of the element. Although the element takes the shape of a portion of a frustocone, it could take the shape of a flat panel, a portion of a tube, an oval, a disk or any other suitable shape. See FIGS. 18A and 18B. Although 4 points of fixation are shown, there be could be more or less fixation. This element could be thin walled and could be made from silicone, a combination of Nitinol and silicone, or other suitable materials or combinations of materials. Preferably, the device is self-expanding and would have adequate structure to impart force against the cardia or upper stomach when fixed at the corners, but would be flexible enough to accommodate peristalsis. Several types of fixation could be used, including and not limited to those previously disclosed. The procedure could be performed gastroscopically by placing the fixation from inside the stomach through the single cardiac member 13, through the stomach wall, and to the outside of the stomach wall on the serosa. Since the device is self-expanding, it may be collapsed for placement down the esophagus and then reforms in the stomach where it can then be fixed into place. As shown in FIGS. 7A and 7B, the fixation element 31 could be an anchor 72 in the form of a t T-bar with a button on one side. This would allow the smooth button to be inside the stomach, and the T-bar to pierce the device and stomach wall. The fixation element 31 could also be an anchor 72 in the form of a collapsible basket as shown in FIGS. 7C an 7D, which then expands to hold the fixation. The fixation element 31 could also be other types of expandable anchors, standard sutures or other types of fixation.

This device could then contain several types of adjustments for adjusting the pressure applied by the single cardiac member to the cardia wall. For example, there could be an inflatable body 27 that could be placed on top of the cardiac portion of the device and against the stomach wall that could be accessed through aninflation element 28. See FIGS. 18A and 18B. This inflation element 28 could be a self-sealing septum of an access port, or the self sealing septum could be incorporated into the balloon surface itself. The inflation element 28 could also be a valve that can be accessed by a blunt ended needle to allow fluid to be added or removed. Similar to the embodiment in FIG. 6A, the inflation element 28 could be connected to the inflation member by a tube 29. This tube could be straight or coiled, with or without a housing, to allow the valve to be pulled up the esophagus and accessed outside the body. As fluid is added, the balloon inflates and compresses the cardia to create a sensation of satiety. After the balloon has been adjusted, the tubing can then retract and be placed back into the stomach. The tubing may be retracted into a housing, which may have a coiling mechanism. The tubing, with or without the housing, is preferably configured to stay in the stomach and not pass through the pylorus. FIGS. 18C and 18E show the inflatable body 27 in the deflated state, while FIGS. 18D and 18F show the inflatable body 27 in the inflated state.

Figure 19:
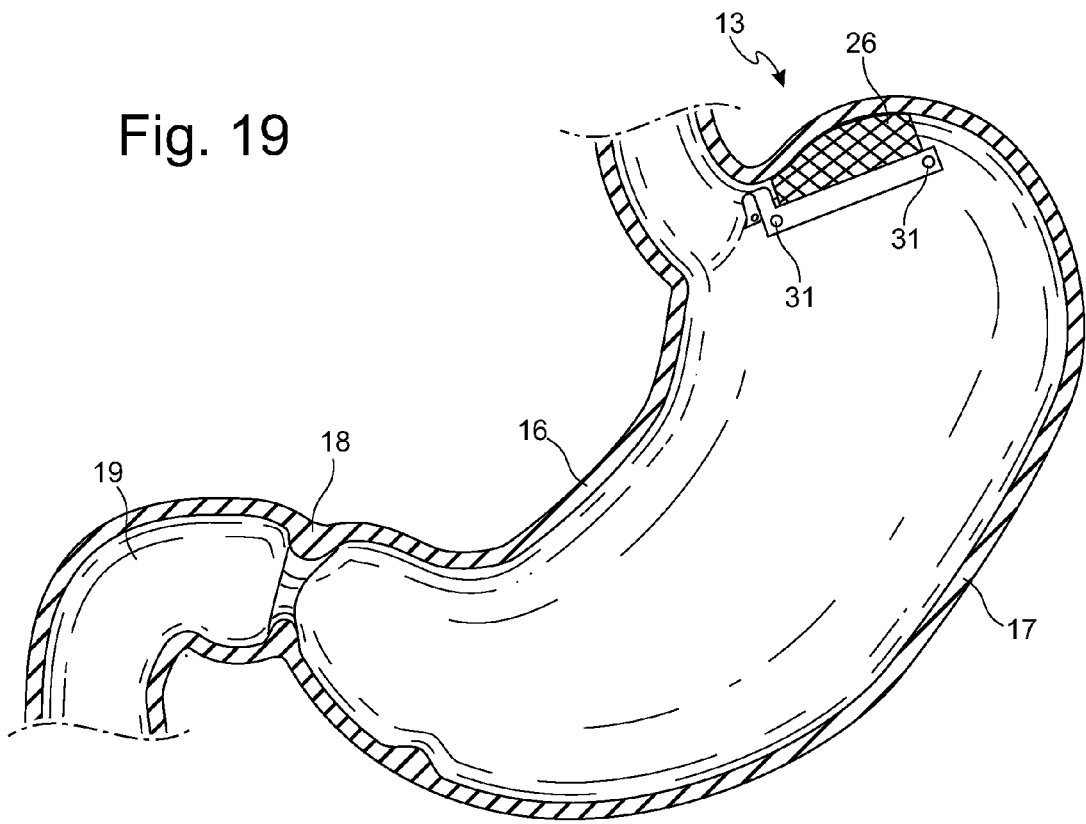
FIG. 19 depicts a side view of an embodiment of a bariatric device of the present invention with an adjustment mechanism, located within a cross-section of a stomach.

Another variation of the embodiment would be to place spacers 26 into a pocket or feature of the single cardiac member 13 to apply outward force for additional pressure against the cardia or upper stomach to adjust the pressure applied by the single cardiac member to the cardia wall. The spacers could be made from solid or hollow sections of polymers, silicone or foam. The spacers could also take the form of shape set self expanding Nitinol features that could apply pressure to the cardia, but accommodate peristalsis. These self expanding Nitinol features could have a variety cross-sectional shapes, angles, and resistance to allow for a range of compression to be applied to the cardia. See FIG. 19. Spacers similar to those shown in 4D and 4E could also be used in this embodiment, but other shapes could also be used. The spacer could be removed endoscopically with a collapsing drawstring and then replaced for a different spacer to change the amount of pressure applied to the cardia.

Figure 20:
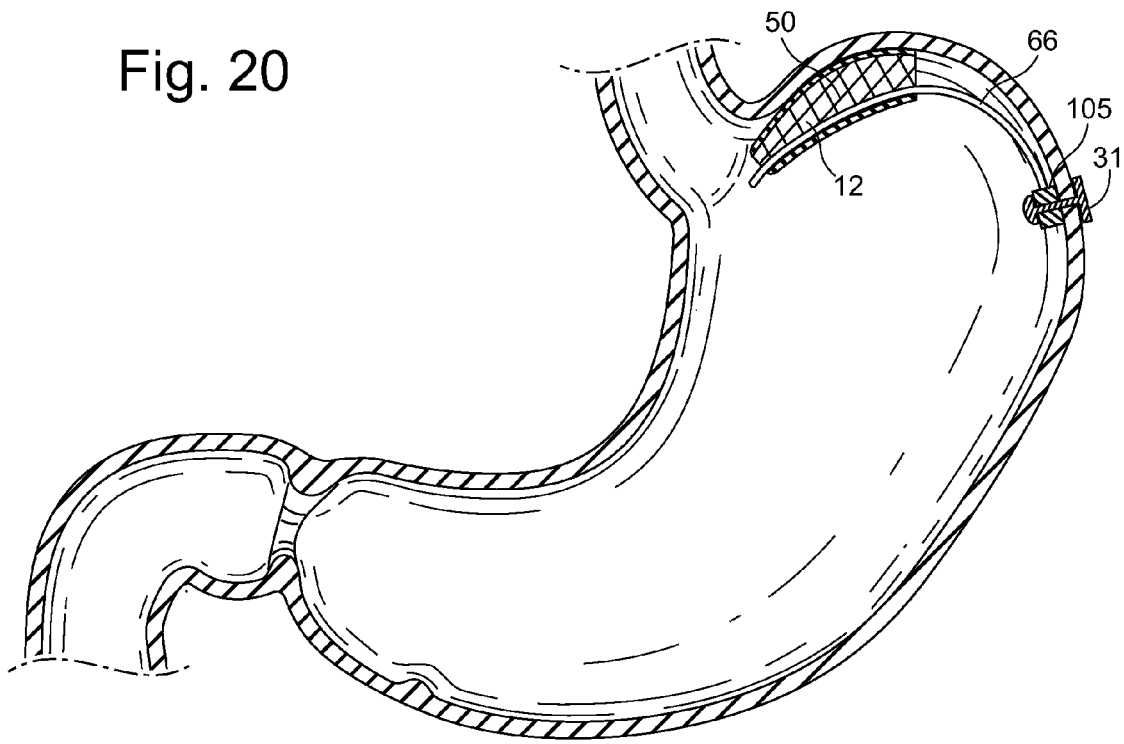
FIG. 20 depicts a side view of an embodiment of a bariatric device of the present invention, located within a cross-section of a stomach.
Figure 23A:
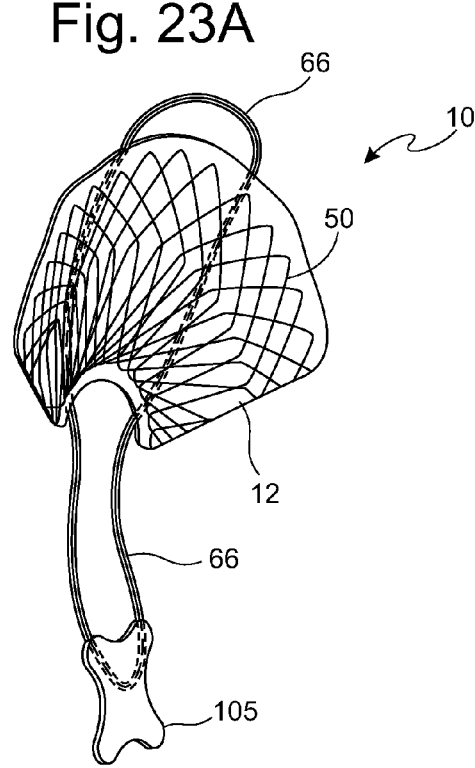
FIG. 23A depicts a backside perspective view of an embodiment of the bariatric device of FIG. 22.
Figure 23B:
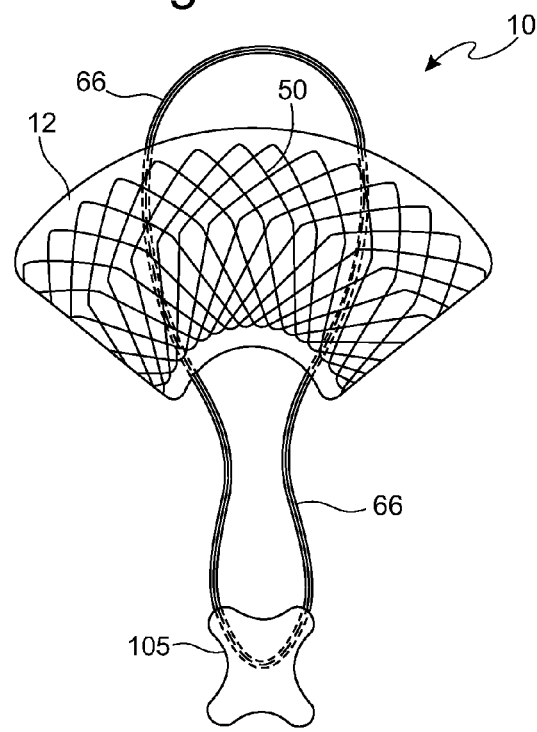
FIG. 23B depicts a front view of an embodiment of the bariatric device of FIG. 22.

In another embodiment, an element may be used to contact the cardia, but may be fixed into place by a fixation element 31 in the fundus, body, or pyloric region of the stomach. This fixation could take place along the lesser curve, greater curve or midline of the stomach. FIG. 20 shows a side view of an embodiment where a cardiac element 12 is positioned at the proximal cardia. This cardiac element 12 is attached to a positioning element 66 which has a connecting joint 105 for attaching a fixation element 31 to fix the device to the stomach wall. The cardiac element is constructed with a self expanding Nitinol wire mesh pattern 50. FIG. 21A shows a backside perspective view of this device and FIG. 21B shows a front view of this device. Preferably, the cardiac element is made of a self expanding structure to maintain its form in the stomach while accommodating peristalsis. The positioning elements are also preferably made from a shape memory or super elastic material to maintain structure while accommodating peristalsis. With self expanding elements, the device may be collapsed for placement down the esophagus and then expand once in the stomach for fixation to the stomach wall. FIG. 22 shows a side view of an alternative embodiment where the positioning element 66, connecting joint 105, and fixation element 31 are located along the lesser curve. FIGS. 23A and 23B show a backside perspective view and front view of this embodiment. Adjustability, sensors, remote control and all other improvements and features previously disclosed herein apply to this embodiment.

Figure 24A:
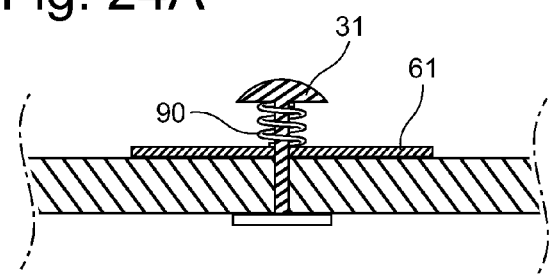
FIG. 24A depicts a side view of an embodiment of a bariatric device of the present invention with an adjustment mechanism in the unexpanded state.
Figure 24B:
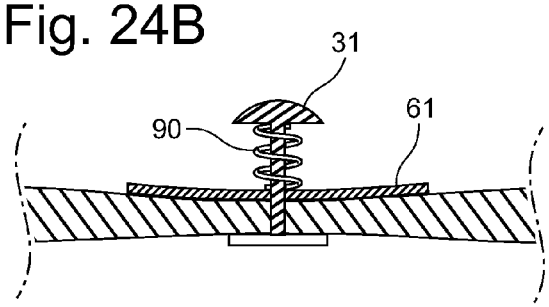
FIG. 24B depicts a side view of an embodiment of a bariatric device of the present invention with an adjustment mechanism in the expanded state.

The bariatric device may have an adjustment element that is equipped with a temporary expansion/contraction element 90 that may allow for temporary adjustment based on activation of a material property, sensor 88 or mechanism of the device. This could be applied to any of the above-discussed embodiments. FIGS. 24A shows a cardiac element in the unexpanded state and 24B shows the cardiac element in the expanded state. It may be desirable for the temporary expansion/contraction element 90 to adjust only upon eating, and then retract after eating. It may be desirable for the device to adjust upon eating and then retract after eating. It may be desirable for the device to adjust with the pH cycle of the patient where pH will be higher prior to eating and then lower after eating. This would allow for intermittent stimulation of the stretch receptors to avoid receptor fatigue over time. For example, the material could be heat sensitive using materials such as Nitinol, which could expand after consuming a cold or hot liquid. The time and duration of the adjustment could be varied up on the desired response.

Similarly, the device could have a sensor 88 or material that is pH or glucose sensitive or detect the presence of food, which could activate the temporary expansion/contraction element 90 to expand when a certain threshold for pH has been reached or glucose, carbohydrates, protein or fat is present after eating. Similarly, this temporary expansion/contraction element 90 could be activated by a magnetic field such as swallowing a magnetic pill that could temporarily expand the device. In this example, the magnetic pill would be small enough and shaped appropriately for passage through the gastrointestinal tract, and be biocompatible. The patient could consume the electromagnetic pill when a satiety signal was desired. It may also be desirable for the device to adjust based on time or sleep cycle such that the device 10 adjusts at specific times of the day or when the patient lays horizontal. Other parameters or mechanisms to trigger the temporary expansion could be used.

Another alternative would be to suspend these devices from either the left or right crura of the diaphragm, or both instead of fixing directly to the stomach wall or esophageal wall.

Devices for Placement with a Gastric Band or Gastric Bypass

Figure 25:
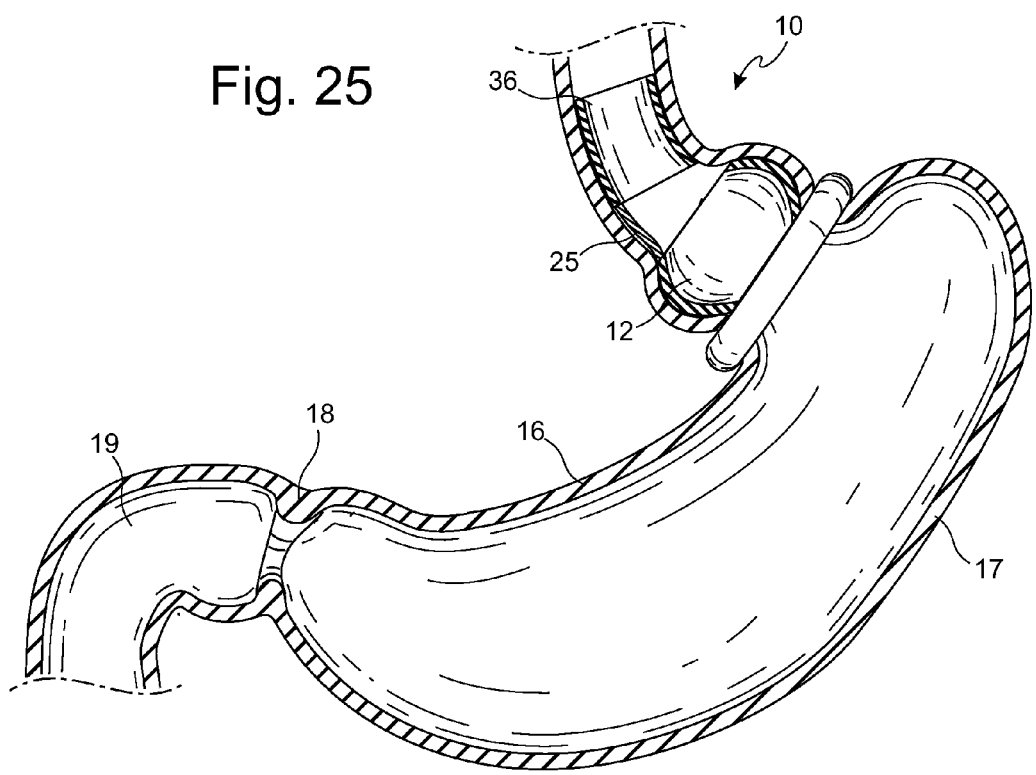
FIG. 25 depicts a side view of an embodiment of a bariatric device of the present invention, located within a cross-section of a stomach.
Figure 26:
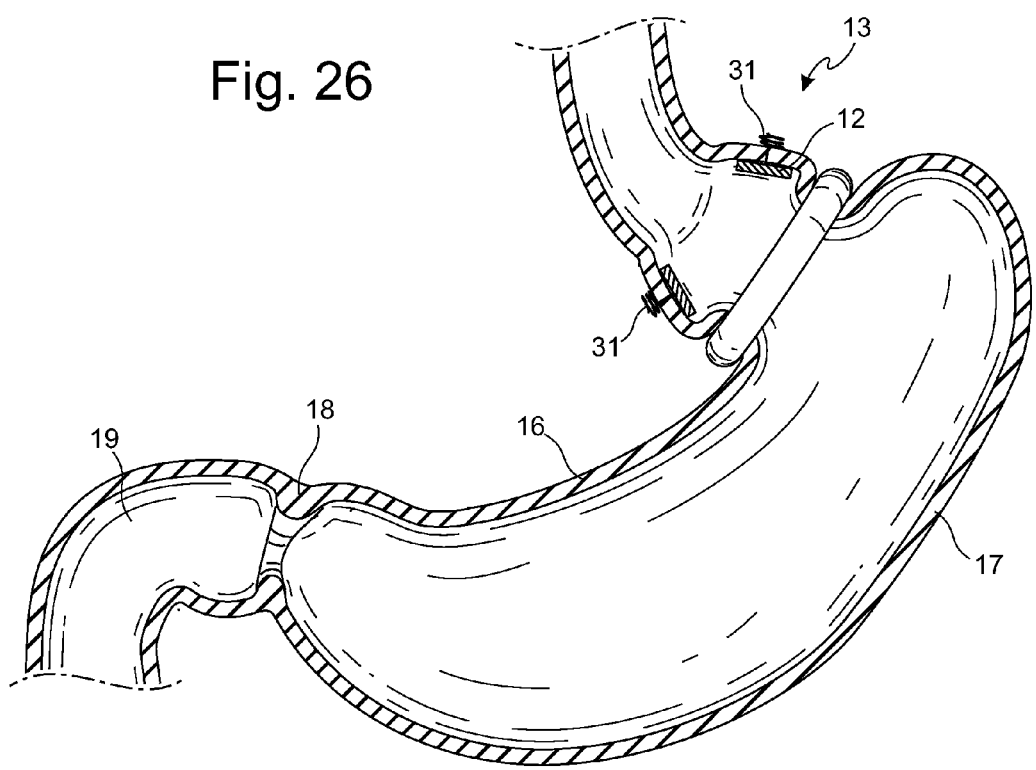
FIG. 26 depicts a side view of an embodiment of a bariatric device of the present invention, located within a cross-section of a stomach.
Figure 27:
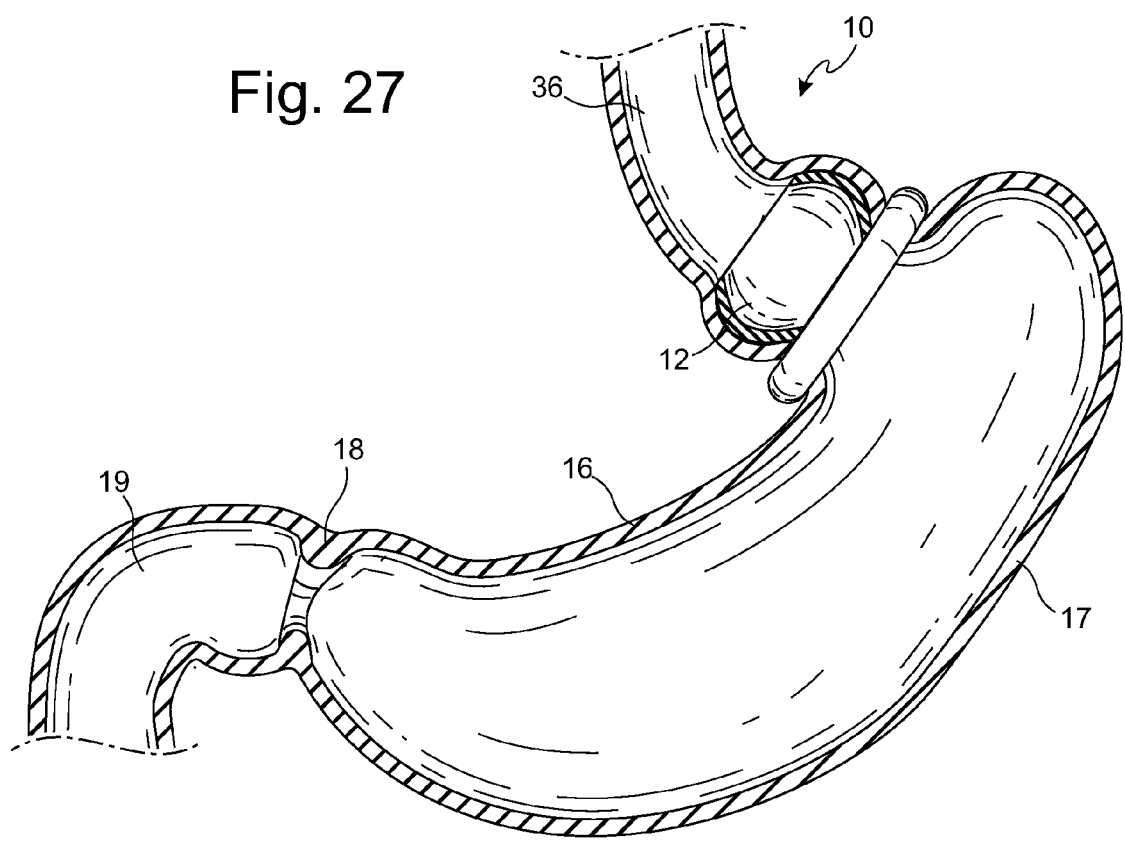
FIG. 27 depicts a side view of an embodiment of a bariatric device of the present invention, located within a cross-section of a stomach.

All of these devices could be modified for use with a gastric band or bypass patient. See FIGS. 25, 26 and 27. FIG. 25 shows a 3 element embodiment with a gastric band. This may be desirable in a patient with a gastric band or bypass where the weight loss has slowed or weight gain has started. In all cases, the devices may need to be sized appropriated to fit within the reduced size of a gastric bypass or gastric band pouch. Although the figures show a gastric band, it is intended to also represent a reduced pouch size of a gastric bypass, a sleeve gastrectomy or other bariatric procedure. Due to the reduced lumen or constriction of the gastric band or bypass below the pouch, the device may be placed without fixation into the stomach wall. FIG. 26 shows how a single cardiac member 13 could be used with a small pouch. FIG. 27 shows an embodiment where a cardiac element 12 could be placed above the gastric band to contact the cardia or upper stomach. This also shows that the geometry is large enough to prevent migration of the device past the band. The embodiment shows a spherical profile or ellipsoid profile to better match the pouch geometry, but other shapes and profiles could be used. This device could be placed temporarily and could be replaced by different shapes or sizes. This feature would be particularly interesting for failed gastric bypass patients who do not have the opportunity for a reversal or for gastric band patients who do not want to undergo surgery, but want to stimulate satiety. This device could be made from silicone, polymers, Nitinol or a combination of any of these. Preferably, this device is made from a self expanding structure to provide pressure against the cardia, but accommodate peristalsis. Self expansion would also allow the device to compressed for placement down the esophagus and then expand into its operational shape and collapse for retrieval.

Placement

As mentioned above, a tube, catheter, or sheath may be required to protect the anatomy during placement of the device down the esophagus and into the stomach. For the small single cardiac embodiments, a sheath may not be required due to the small size. Where protection is require, it could be a simple flexible tube to aid in straightening and compressing the device while it is being introduced. Insertion of the device into the tube would require compression of the device into a narrow, streamlined shape. A standard gastroscopic tool could be used to push or pull the device down the tube. Similarly, a custom gastroscopic tool or sheath could be used to introduce the device into the stomach through the esophagus or other narrow opening.

Removal

For removal, a flexible tube such as a standard overtube could be used with a standard or custom endoscopic tool. The tube may be placed down the esophagus and the tool then placed down the lumen of the overtube. Endoscopic scissors or cautery could be used to cut fixation where necessary and a standard grasper or snare could grasp the device and pull it up the tube. The device would be straightened by the overtube for removal from the stomach and esophagus. The device may be flexible and small enough in profile to pull up the overtube with a standard grasper.

In another embodiment, the elements may incorporate a collapsing mechanism designed to collapse the element into a compact shape for removal. For example, a constriction member comprising a wire or thread may be sewn spirally around, through, or inside the length of one of the elements. The ends of the constriction member may be connected. When the constriction member is pulled, it tightens the circumference of the element like a drawstring, which collapses the element down to a narrow profile that can be safely removed through the esophagus or other narrow opening, or ease its placement into a tube for removal. The constriction member could be made from Nitinol, stainless steel wire, polypropylene, PTFE thread, EPTFE thread or PTFE coated threads or other suitable materials. The constriction member could be integrated into the elements in a variety of patterns such as a continuous spiral, two spirals of reversing orientation, a single loop or other.

The foregoing description of the preferred embodiments of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

INDUSTRIAL APPLICABILITY

This invention may be industrially applied to the development, manufacture, and use of bariatric devices for weight loss purposes.

What is claimed is:

1. A bariatric device for achieving weight loss, comprising:
   a. a cardiac element adapted to be positioned within a stomach at a cardiac region of the stomach, and when so positioned applies at least intermittent outwardly directed pressure from within the stomach to the cardia wall, the cardiac element comprising a frustoconical surface defining a first opening having a first diameter at a proximal end and defining a second opening having a second diameter larger than the first diameter at a distal end, wherein the frustoconical surface is configured to extend between the proximal and distal ends along the cardiac region;
   b. a fixation element connected to the cardiac element and configured to prevent migration of the cardiac element away from the cardiac region of the stomach;
   c. an esophageal element, separate and dis-contiguous from the cardiac element, the esophageal element configured for positioning within the esophagus above and in spaced relation from the cardiac element, the esophageal element connected to the fixation element; and
   d. an adjustment element adapted to be positioned within the stomach and which is adapted to adjust the pressure applied by the cardiac element to the cardia wall, including a modular stiffening member formed as a ring surrounding the first opening, the ring is configured to be disposed between the cardiac element and the cardia wall, wherein the ring is configured as a spring having one end connected to the cardiac element and a second end, opposite the first end, that is configured to be biased to engage the cardia wall to adjust the pressure applied thereto, wherein the adjustment element is configured to flex, and wherein the ring is disposed completely on an outer surface of the cardiac element.

2. The bariatric device according to claim 1, wherein the ring has a generally teardrop shape.

3. The bariatric device according to claim 1, wherein the modular stiffening member is configured to flex to the curvature of the cardia wall.

4. The bariatric device according to claim 1, wherein the modular stiffening member is configured to bias the cardiac element against the cardia wall.

5. The bariatric device according to claim 1, wherein the frustoconical surface is a solid surface.

6. The device according to claim 1, wherein the fixation element is adapted to extend through the walls of the esophagus and the stomach.

7. A bariatric device for achieving weight loss, comprising:
   a cardiac element adapted to be positioned within a stomach at a cardiac region of the stomach, and when so positioned applies at least intermittent outwardly directed pressure from within the stomach to the cardia wall, the cardiac element comprising a convex surface defining a first opening having a first diameter at a proximal end and defining a second opening having a second diameter larger than the first diameter at a distal end, wherein the convex surface is configured to extend between the proximal and distal ends along the cardiac region;
   a fixation element configured to prevent migration of the cardiac element away from the cardiac region of the stomach;
   an esophageal element, separate and dis-contiguous from the cardiac element, the esophageal element configured for positioning within the esophagus above and in spaced relation from the cardiac element, the esophageal element connected to the fixation element; and
   an adjustment element adapted to be positioned within the stomach and which is adapted to adjust the pressure applied by the cardiac element to the cardia wall, including a modular stiffening member replaceably connected to the cardiac element, and wherein the modular stiffening member being disposed completely on an outer surface of the cardiac element, the modular stiffening member is configured to be disposed between the cardiac element and the cardia wall, and the modular stiffening member conforming to the curvature of the convex surface, the modular stiffening member formed as a spring having one end connected to the cardiac element and a second end, opposite the first end, that is configured to be biased to engage the cardia wall to adjust the pressure applied thereto, wherein the adjustment element is configured to flex.

8. The device according to claim 7, wherein the modular stiffening element is disposed between the proximal end and the distal end of the convex surface.

9. The device according to claim 7, wherein the convex surface is a solid surface.

10. A bariatric device for achieving weight loss, comprising:
    a cardiac element adapted to be positioned within a stomach at a cardiac region of the stomach, and when so positioned applies at least intermittent outwardly directed pressure from within the stomach to the cardia wall, the cardiac element comprising a tapered surface defining a first opening having a first diameter at a proximal end and defining a second opening having a second diameter larger than the first diameter at a distal end, wherein the tapered surface is configured to extend between the proximal and distal ends along the cardiac region;
    a fixation element configured to prevent migration of the cardiac element away from the cardiac region of the stomach;
    an esophageal element, separate and dis-contiguous from the cardiac element, the esophageal element configured for positioning within the esophagus above and in spaced relation from the cardiac element, the esophageal element connected to the fixation element; and
    an adjustment element adapted to be positioned within the stomach and which is adapted to adjust the pressure applied by the cardiac element to the cardia wall, including a modular stiffening member replaceably connected to the cardiac element, and wherein the modular stiffening member being disposed completely on an outer surface of the cardiac element, the modular stiffening member is configured to be disposed between the cardiac element and the cardia wall, and the modular stiffening member conforming to the tapered surface, the modular stiffening member formed as a spring having one end connected to the cardiac element and a second end, opposite the first end, that is configured to be biased to engage the cardia wall to adjust the pressure applied thereto, wherein the adjustment element is configured to flex.

11. The device according to claim 10, wherein the modular stiffening member is disposed between the proximal end and the distal end of the tapered surface.

12. The device according to claim 10, wherein the tapered surface is a solid surface.

* * * * *